United States Patent
Scott et al.

(10) Patent No.: US 11,694,779 B2
(45) Date of Patent: Jul. 4, 2023

(54) SYSTEMS AND METHODS FOR AUTOMATED REPORTING AND EDUCATION FOR LABORATORY TEST RESULTS

(71) Applicant: LabSavvy Health, LLC, Falls Church, VA (US)

(72) Inventors: Cary Scott, Falls Church, VA (US); Farrukh Hameed, Falls Church, VA (US); Fisnik Shpuza, Reston, VA (US)

(73) Assignee: LabSavvy Health, LLC, Falls Church, VA (US)

( * ) Notice: Subject to any disclaimer, the term of this patent is extended or adjusted under 35 U.S.C. 154(b) by 277 days.

(21) Appl. No.: 16/573,691

(22) Filed: Sep. 17, 2019

(65) Prior Publication Data

US 2020/0090801 A1 Mar. 19, 2020

Related U.S. Application Data

(60) Provisional application No. 62/732,451, filed on Sep. 17, 2018.

(51) Int. Cl.
| | |
|---|---|
| *G16H 15/00* | (2018.01) |
| *G06T 11/20* | (2006.01) |
| *G06T 11/60* | (2006.01) |
| *G06F 3/0482* | (2013.01) |

(52) U.S. Cl.
CPC .......... *G16H 15/00* (2018.01); *G06T 11/206* (2013.01); *G06T 11/60* (2013.01); *G06F 3/0482* (2013.01)

(58) Field of Classification Search
CPC ........ G16H 15/00; G16H 10/40; G16H 10/60; G06T 11/206; G06T 11/60
See application file for complete search history.

(56) References Cited

U.S. PATENT DOCUMENTS

| | | | |
|---|---|---|---|
| 8,812,241 B1* | 8/2014 | Markin | G16H 10/40 |
| | | | 702/19 |
| 10,497,076 B2* | 12/2019 | Darguesse | G16H 40/60 |
| 2007/0179347 A1 | 8/2007 | Tarassenko et al. | |
| 2007/0198301 A1 | 8/2007 | Ayers et al. | |
| 2011/0046973 A1 | 2/2011 | Goodnow et al. | |

(Continued)

OTHER PUBLICATIONS

International Searching Authority, International Search Report and Written Opinion, issued for International Application No. PCT/US2019/051540, dated Nov. 22, 2019 (15 pages).

*Primary Examiner* — Alvin H Tan
(74) *Attorney, Agent, or Firm* — Polsinelli PC; David R. Mika

(57) ABSTRACT

Systems and methods for providing test results include receiving a request from a user computing device for historical test result data associated with a patient for a test type at a computing system. In response to receiving the request, the computing system accesses the historical test result data for the patient and test type, which includes a test result value and a test range. The computing system generates graphical data, in part, by normalizing the historical test result data by fitting the test range to a chart subrange corresponding to a predetermined range for the test result (e.g., a normal outcome of the test). The computing system then transmits the graphical data to the user computing device for rendering and display at the user computing device.

13 Claims, 27 Drawing Sheets

(56) References Cited

U.S. PATENT DOCUMENTS

2014/0095193 A1    4/2014   Rangarajan et al.
2015/0073815 A1*   3/2015   Holmes ................. G16H 10/40
                                                                          705/2

* cited by examiner

SYSTEMS AND METHODS FOR AUTOMATED REPORTING AND EDUCATION FOR LABORATORY TEST RESULTS

CROSS-REFERENCE TO RELATED APPLICATION

This application is related to and claims priority under 35 U.S.C. § 119(e) from U.S. Patent Application No. 62/732,451, filed Sep. 17, 2018 entitled "Systems and Methods for Automated Reporting and Education for Laboratory Test Results," the entire contents of which is incorporated herein by reference for all purposes.

TECHNICAL FIELD

Aspects of the present disclosure relate to a system for managing lab test results and related healthcare information and for providing related information and educational materials.

BACKGROUND

Electronic collection and storage of medical information, such as lab results, has led to improved availability of and access to such information for patients and healthcare professionals alike. However, correctly interpreting such information to implement meaningful and effective healthcare strategies remains a difficult task with potential implications for a patient's short- and long-term health.

In the context of lab tests, analysis and interpretation of historical test results are complicated by various factors. For example, lab results from different labs may be stored in different systems and have different formats, thereby complicating the task of aggregating results from different labs. As another example, different pieces of lab equipment for performing a given test may generate data in different formats or may be calibrated differently (e.g., may consider different ranges of values to be "normal"). Moreover, even if historical lab results can be obtained, analyzing such results and determining an appropriate course of action is a difficult task in and of itself.

It is with these observations in mind, among others, that aspects of the present disclosure were conceived.

SUMMARY

In one aspect of the present disclosure, a method of providing test results is provided. The method includes receiving, at a computing system and from a user computing device, a request for historical test result data associated with a patient, the request including a test type. In response to receiving the request, the computing system accesses historical test result data associated with the patient for the test type, the historical test result data including each of a test result value for a test of the test type and a test range for the test. The method further includes accessing chart data associated with the test type using the computing system, the chart data including a total chart range and a chart subrange. The chart subrange is a portion of the total chart range corresponding to the test range. The method further includes generating, at the computing system, graphical data for displaying the historical test result data at the user computing device. The graphical data is generated, at least in part, by calculating a location for displaying an indicator for the test result value relative to the total chart range. To do so, the computing system normalizes the historical test result data by fitting the test range to the chart subrange. The computing system then transmits the graphical data to the user computing device for rendering and display at the user computing device.

In one implementation, fitting the test range to the chart subrange includes at least one of scaling and offsetting to the test range to the chart subrange.

In another implementation, the test may be a first test such that the test result value is a first test result value and the test range is a first test range. In such implementations, the historical test result data may further includes a second test result value for a second test and a second test range for the second test and the graphical data may further include a second location for displaying a second indicator relative to the total range, the second indicator corresponding to the second test result value. Also in such implementations, generating the graphical data may further include calculating the second location by normalizing the historical test result data by fitting the second test range to the chart subrange. In certain cases, the first test range and the second test range may be different.

In yet another implementation, the location of the indicator and fitting of the test range to the chart subrange may be performed using a predetermined formula. For example, in one implementation, calculating the location and fitting the test range to the chart subrange may be performed using the following equation:

$$x_{chart} = \frac{(x_{test} - B_{test})}{R_{test}/R_{chart}} + B_{chart}$$

where: $x_{template}$ is the location of the indicator relative to the total range, $x_{test}$ is the test result value, $R_{test}$ is a magnitude of the test range, $R_{chart}$ is a magnitude of the chart subrange, $B_{test}$ is a threshold value for the test range, and $B_{chart}$ is a threshold value for the chart subrange corresponding to the threshold value for the test range.

In another implementation, the method further includes receiving test result data at the computing system from a healthcare data system and storing the test result data in one or more data sources of the computing system as part of the historical test result data. In such implementations, the test result data may be received through a translation layer between the computing system and the healthcare data system that converts the test result data into a common format for storage in the one or more data sources.

In other implementations, each of the test range and the chart subrange correspond to a normal result range for the test type.

In still other implementations, the chart subrange corresponds to an intermediate range of the total range such that the chart includes at least three visually delineated ranges. The at least three visually delineated ranges may include, for example, a first visually delineated range corresponding to the chart subrange, a second visually delineated range corresponding to values below the first visually delineated range, and a third visually delineated ranges corresponding to values above the first visually delineated range.

In another implementation, the chart subrange may correspond to one of an upper range and a lower range of the total range such that the chart includes at least two visually delineated ranges. The at least two visually delineated ranges may include, for example, a first visually delineated range corresponding to the chart subrange and a second visually delineated range corresponding to values above the first visually delineated range when the template range is the lower range or values below the first visually delineated range when the template range is the upper range.

In still other implementations, the method may further include, subsequent to transmitting the graphical data to the user computing device, receiving, at the computing system and from the user computing device, a message including an identifier corresponding to a graphical element of the chart. In response to receiving the message, the computing system transmits at least one of additional test result data corresponding to the test or content associated with the test to the user computing device.

In another aspect of the present disclosure, a computing system is provided. The computing system includes one or more processors and a memory storing instructions executable by the one or more processors. When executed by the one or more processors, the instructions cause the one or more processors to receive, from a user computing device, a request for historical test result data associated with a patient, the request including a test type. The instructions further cause the one or more processors to access, in response to receiving the request, historical test result data associated with the patient for the test type, the historical test result data including a test result value for a test of the test type and a test range for the test. The instructions further cause the one or more processors to access chart data associated with the test type, the chart data including a total chart range and a chart subrange, the chart subrange being a portion of the total chart range corresponding to the test range and to generate graphical data for displaying the historical test result data at the user computing device. Generating the graphical data includes calculating a location for displaying an indicator for the test result value relative to the total chart range by normalizing the historical test result data of the test. Such normalization generally includes fitting the test range to the chart subrange. The instructions further cause the one or more processors to transmit the graphical data from the computing system to the user computing device for rendering and display at the user computing device In at least some implementations, fitting the test range to the chart subrange comprises at least one of scaling and offsetting the test range such that the test range corresponds to the chart subrange.

In other implementations, the test is a first test such that the test result value is a first test result value and the test range is a first test range. In such implementations, the historical test result data may further include a second test result value for a second test and a second test range for the second test and the graphical data may further include a second location for displaying a second indicator relative to the total range, the second indicator corresponding to the second test result value. Also in such implementations, generating the graphical data may further include calculating the second location by normalizing the historical test result data, including fitting the second test range to the chart subrange. In such implementations, the first test range and the second test range are different.

In still other implementations, each of the test range and chart subrange may correspond to a normal result for the test type.

In yet another aspect of the present disclosure, a method of accessing and displaying test results is provided. The method includes transmitting, from a user computing device, a request for historical test result data associated with a patient to a remote computing system, the request including a test type. The method further includes receiving, at the user computing device and from the remote computing system, graphical data for rendering and displaying a chart of the historical test result data. The graphical data is generated by the remote computing device and includes an indicator location for displaying an indicator relative to a total range of a chart. The indicator corresponds to a test result value of a test included in the historical test result data. The indicator location is calculated by the remote computing device by normalizing the historical test result data of the test by fitting a test range corresponding to the test to a chart subrange of the chart, the chart subrange being a portion of a total range of the chart corresponding to the test range. The method further includes, in response to receiving the graphical data, rendering the graphical data using the user computing device to display the chart on a display of the user computing device, the chart including the indicator at the indicator location.

In certain implementations, the indicator location may be one of a plurality of indicator locations included in the graphical data, each of the plurality of indicator locations associated with a respective test result value of a respective test of the test type. In such implementations, each indicator location may be calculated by the remote computing device by normalizing the historical test result data of the respective test by fitting a respective test range corresponding to the respective test to the chart subrange. Also in such implementations, rendering the graphical data may include displaying a respective indicator at each of the plurality of indicator locations.

In other implementations, rendering the graphical data may further include displaying a most recent test result value adjacent a most recent indicator.

In still other implementations, the chart may include a plurality of visually delineated ranges, one of the visually delineated ranges corresponding to the chart subrange.

In yet other implementations, the method may further include receiving a selection of a graphical element of the chart at the user computing device and transmitting a request to the remote computing device including an identifier associated with the graphical element. In such implementations, the method may further include receiving, from the remote computing device, at least one of additional details of the test and informational content selected by the remote computing device.

BRIEF DESCRIPTION OF THE DRAWINGS

The foregoing and other objects, features, and advantages of the present disclosure set forth herein will be apparent from the following description of particular embodiments of those inventive concepts, as illustrated in the accompanying drawings. Also, in the drawings the like reference characters refer to the same parts throughout the different views. The drawings depict only typical embodiments of the present disclosure and, therefore, are not to be considered limiting in scope.

FIGS. 4A-4I are a first set of screenshots of an example user interface illustrating manual input of test results for a system according to the present disclosure.

FIGS. 5A-5G are a second set of screenshots of an example user interface illustrating a process for ordering tests through a system according to the present disclosure.

FIGS. 6A-6E are third set of screenshots of an example user interface illustrating access and review of patient records through a system according to the present disclosure.

DETAILED DESCRIPTION

Figure 1:
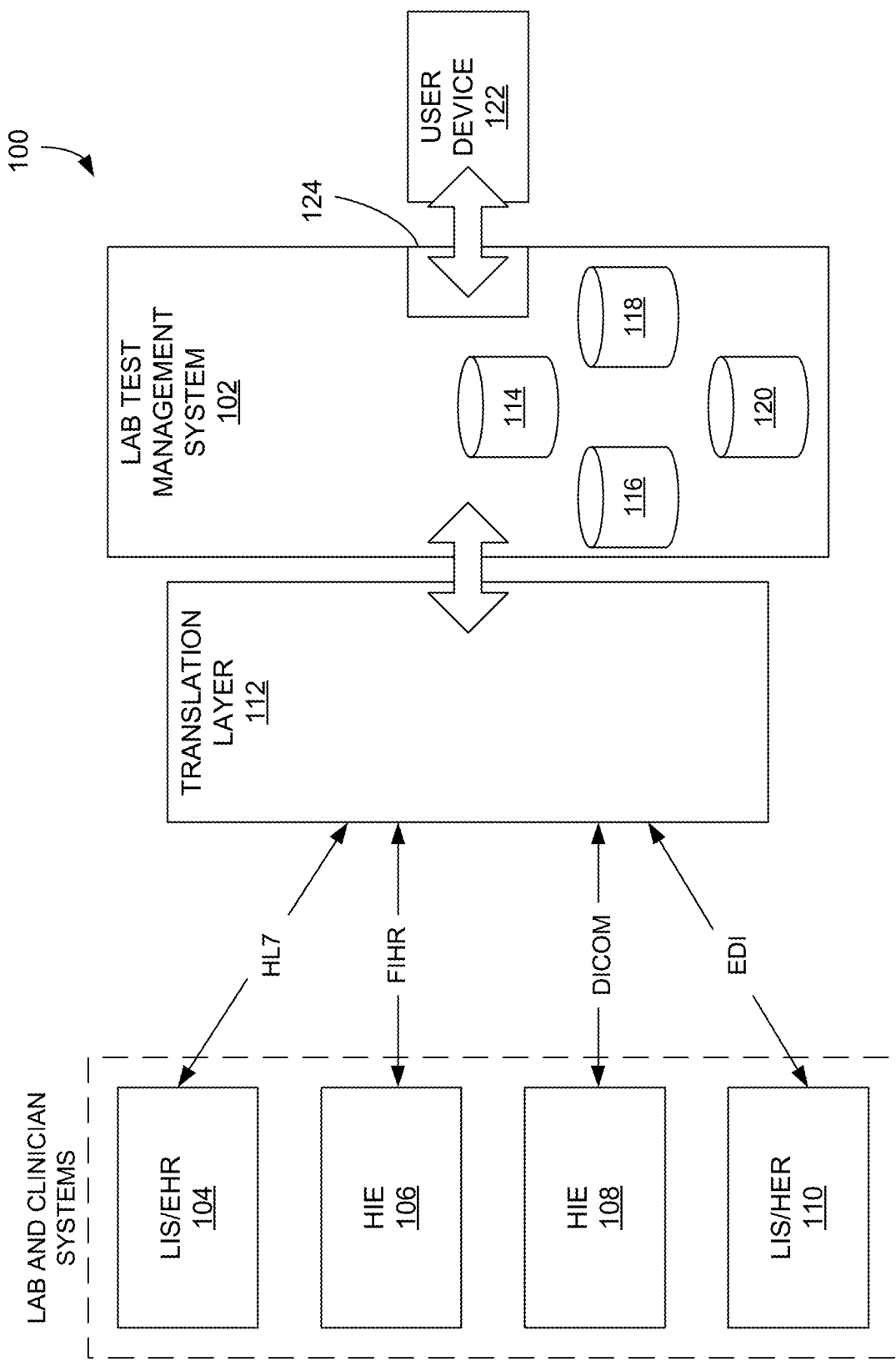
FIG. 1 is a block diagram illustrating an example lab result processing system in accordance with one implementation of the present disclosure.

Aspects of the present disclosure are directed to computer-based systems for facilitating communication of lab results and associated medical and educational information. The systems disclosed herein improve the ease and clarity with which lab-related information is conveyed between interested parties such as patients, healthcare providers who may order tests for such patients, and laboratories that may conduct such tests. In general, systems in accordance with the present disclosure include one or more computing devices adapted to collect and store laboratory result and other health-related information from one or more healthcare data systems and to present such data to patients, healthcare providers, and laboratory employees in a meaningful manner.

Systems described herein include one or more computing devices implementing a portal, application, website, or similar environments adapted to facilitate the exchange of lab results and associated information between users of the system. Such users may include patients, healthcare providers, and laboratories, which may access the system using a range of computing devices including, without limitation, one or more of desktop/laptop computers, tablets, smartphones, and the like. Depending on the nature of the user, the system may provide different features and functionality. For example, patients may generally use the system to access and review scheduled tests and results of previously conducted tests. In certain implementations, the system may also include a library or similar repository of content that may be accessible to a patient to provide the patient with additional education or information regarding particular tests or conditions. Such additional information may include details regarding a test (e.g., preparation required, the process of administering the test), general guidelines regarding the interpretation of test results, and subsequent steps that may be taken by the patient based on test results. In certain implementations, the system may automatically and intelligently curate, select, or customize content based on the particular test undergone by a patient and/or the results of any such tests. The system may also provide a platform for secure and Health Insurance Portability and Accountability Act (HIPAA)-compliant communication between patients and their healthcare providers. The material provided through the system may be obtained from external sources, such as external websites or medical information databases, or may be custom materials generated by a host of the system or practitioners using the system. Such custom material may be beneficial in providing simplified or "layman's" summaries of test and corresponding results.

From the perspective of healthcare providers and laboratories, systems in accordance with the present disclosure may similarly enable access to test results and related information, but may also provide a platform through which tests may be ordered or procured. In certain implementations, healthcare providers may also access or otherwise select the educational content available through the system to select or otherwise identify material relevant to a particular patient.

Through the systems and methods disclosed herein, patients are provided prompt access to test results, reducing anxiety associated with long delays in receiving such results. Patients are also better able to track and monitor their tests through the system, which can consolidate test results from multiple laboratories and/or healthcare providers into a single platform that is readily accessible by patients using a variety of devices. Patients further benefit from the educational resources available through the system, particularly when such resources are curated or customized by a physician or by intelligence incorporated into the system based on the patient's characteristics or history, and direct HIPAA-compliant communication with physicians or lab consultants facilitated through the platform.

The system and methods herein also provide a range of benefits to clinicians. For example, the system enables seamless execution of lab tests throughout various stages from ordering of such tests and communication of results to the patient to instructing the patient regarding subsequent steps or providing additional education. In certain implementations, systems in accordance with the present disclosure may also include a range of automated features that are currently unsupported by conventional healthcare data systems. For example, the system may provide built-in risk calculations or similar metrics to assist physicians in evaluating the benefits of performing particular tests. As previously noted, communication between clinicians and patients is also facilitated through HIPAA-compliant voice and text communication through the system, providing clinicians with flexibility and ultimately saving time with patient interactions. The system may also support automatic documentation and reporting of billable patient interactions and consultations, enabling improved recordkeeping and accounting.

Similar to clinicians, labs and their personnel further benefit from the seamless execution of tests provided through the system of the present disclosure. From receiving an order for a test through performance of the test, communication of test results to clinicians/patients, and provisioning of corresponding information or educational material, the system provides lab facilities with a fast and easy way of managing the tests they perform.

In certain implementations of the present disclosure, the system may be configured to generate flag or alert statements in response to receiving test results. Such statements may be provided to a patient when the patient logs into the system or may be delivered through the system by messaging functionality of the system.

As previously noted, systems in accordance with the present disclosure may include a HIPAA-compliant messaging platform to facilitate communication between patients and healthcare practitioners. Such messaging may take various forms including in-system mail, chats, voice messages, video messages, and the like. In certain implementations, communications between practitioners and patients may be automatically logged and recorded as notes associated with a given test or report, thereby streamlining recordation.

In certain implementations, the system may also track and record patient interaction with the system to ensure that the patient has received and reviewed test results or other materials. Such confirmation may be used to meet various regulations and standards related to patient communication including, without limitation, HIPAA compliancy, meaningful user requirements, Medicare Access and CHIP Reauthorization Act (MACRA) requirements, and Merit Based Incentive Payments System (MIPS) requirements.

FIG. 1 is a block diagram illustrating an example lab result processing system 100 in accordance with one implementation of the present disclosure. In general, the system 100 includes a lab test management system 102 that facilitates retrieval of lab results and other patient information from lab and clinical systems, stores the retrieved data, and presents lab results and associated information to users, such as through a website or application executed on a computing device of the user. The lab test management system 102 may be implemented in various ways, but may generally include one or more computing devices or virtual machines communicatively coupled to each other and configured to provide the various functions described herein. Further details regarding possible computing devices that may be used to implement the lab test management system 102 are provided in the context of FIG. 7 and the corresponding discussion, below.

Lab result information may be obtained by the lab test management system 102 from one or more lab or clinical data systems 104-110. In general, the data systems 104-110 may take various forms but, in general, provide lab result and patient information to the lab test management system 102. As illustrated in FIG. 1, each of the data systems 104-110 may be one of a laboratory information system (LIS), an electronic health record (EHR) system, a health information exchange (HIE), or any similar data system for providing health-related information.

The format, framework, and protocol by which each of the data systems 104-110 provides its respective data may vary. For example, as illustrated in FIG. 1, the various data systems 104-110 may provide data according to one or more of Health Level 7 (HL7), Fast Healthcare Interoperability Resources (FHIR), Digital Imaging and Communications in Medicine (DICOM), and Electronic Data Interchange (EDI) standards. This list of data standards is merely intended to be illustrative and should be regarded as non-limiting. Rather, it should be appreciated that the lab test management system 102 may interact with and receive data from any health information data systems currently known or later developed.

As data may be collected in various formats and using various protocols, certain implementations of the present disclosure may include a translation layer 112 configured to facilitate communication between the data systems 104-110 and the lab test management system 102. In certain imple-mentations, the translation layer 112 may include one or more devices and/or software modules configured to communicate and receive data from one or more of the data systems 104-110 and to convert the received data into a standardized format for storage and use by the lab test management system 102. In certain implementations, the translation layer 112 may be implemented using a representational state transfer (REST)-based architecture. In other implementations, the translation layer 112 may instead be implemented using one or more remote procedure calls (RPC), web services (such as SOAP or WSDL), or other approaches for facilitating communication between computing devices and/or software modules.

The lab test management system 102 may include, be communicatively coupled or otherwise have access to one or more databases or similar data stores. Such data stores are generally used to store information for use by the lab test management system 102. For example, the system 100 includes each of a user information data store 114, a lab results data store 116, a content data store 118, and a test data store 120.

The user information data store 114 may be populated with information regarding users of the system 100. Such information may include, without limitation, login credentials for users of the system and contact information. Information contained within the user information data store 114 may vary depending on whether the stored data corresponds to a laboratory or clinical user or a patient. For example, a patient's user information may include, among other things, information regarding the patient's employer, insurance policies, billing and payment history, and the like. As another example, if a user is instead an employee or otherwise associated with a healthcare provider, otherwise associated with a lab or clinic user's information may include, among other things, the organization to which the user belongs and licensing or other credential information. The lab results data store 116 may contain lab result data for patient users of the system 102. As previously noted, such lab result data may be obtained from data systems 104-110, but may also be manually provided by patients or healthcare practitioners. The content data store 118 may contain educational or other materials for use by the system 102. Such content may include text, images, videos, audio, or any other similar content that may be used to convey educational or other information to the user.

The test data store 120 may include information regarding tests that may be ordered and managed through the system 102 and associated information for such tests. In certain implementations, the test data store 120 may further include information for grouping certain tests. The groupings may, for example, be used to create panels or similar collections of test that are commonly performed together. The groupings may include commonly performed panels. However, in certain implementations, the system 102 may support practitioners or other users generating custom groupings, thereby enabling the creation of custom panels that more accurately reflect patient needs.

Although illustrated in FIG. 1 as three distinct data objects, the data stores 114-120 may be implemented as more or fewer data objects and, as a result, the implementation illustrated in FIG. 1 is intended merely as a non-limiting example. For example, more or fewer data sources may be used to store data for use by the lab test management system 102 and particular types of data may be stored or otherwise distributed across any number of data sources. In certain implementations, multiple data stores may be used to store the same data to provide redundancy, improved accessibility, or similar benefits. Moreover, while user information, lab results, and content are provided as specific examples of data that may be stored and accessible by the lab test management system 102, it should be appreciated that other implementations of the present disclosure may include the storage, maintenance, and retrieval of other data that may be beneficial to users of the system 100.

It should also be appreciated that the data stores 114-120 are merely examples of databases or other data objects that may be used to implement the system 102. For example, in addition to the user, lab result, and content data discussed above, additional data objects may be implemented to facilitate other functions of the system. For example, the system may store, among other things, details regarding patients, clinical or laboratory organizations, and the like within appropriate data objects.

As illustrated in FIG. 1, the lab test management system 102 is generally accessible through one or more computing devices, such as user computing device 122. As previously noted, the user computing device 122 may be any of a number of computing devices including, without limitation, a smartphone, a tablet, a smartwatch, a laptop computer, a desktop computer, or any other similar computing device. In certain implementations, the user accesses the lab test management system 102 through an application, browser, or similar software executed on the computing device 122 and, in some instances, may be a mobile device that provides fast and easy access to the system 102.

Communication between the lab test management system 102 and the user computing device 122 may be facilitate through one or more application programming interfaces (APIs) 124. In one example implementation, such APIs may rely on JavaScript Object Notation (JSON) or a similar standard to for transmission of data between the lab test management system 102 and the user computing device 122, however, it should be appreciated that communication between the lab test management system 102 and the user computing device 122 may occur using any of a number of communication protocols currently known or hereafter developed.

The API 124 may support a variety of functions to facilitate interaction between the lab test management system 102 and the user computing device 122. The following examples are merely illustrative of functions and subroutines that may be included in the API 124 and should not be seen as limiting.

A first component of the API 124 may be used to facilitate user authentication. Such a component may include functionality for authorizing a user, such as by verifying login and password information provided by the user. The API 124 may further support registration and pre-registration of a user, the latter including transmission and verification of an authorization number or similar verification token that may be transmitted to a user by text message, phone, or other communication method.

The API 124 may further support general account management functions, such as password changes, password resets, and retrieval and updating of user information. In certain implementations, such functionality may also include managing information regarding organizations (e.g., clinics or lab facilities) to which a user may belong. Such management may include adding or removing users from an organization and setting permissions for users within an organization. The API 124 may also support functions for obtaining test information (such as from the lab test data store 120) to facilitate ordering of tests for a particular patient.

The API 124 may also include functions directed to the retrieval of patient information. Such information may include general profile information for a patient, recent test results, historical test results, or any other similar data that may be stored and maintained within the system 102.

Figure 2A:
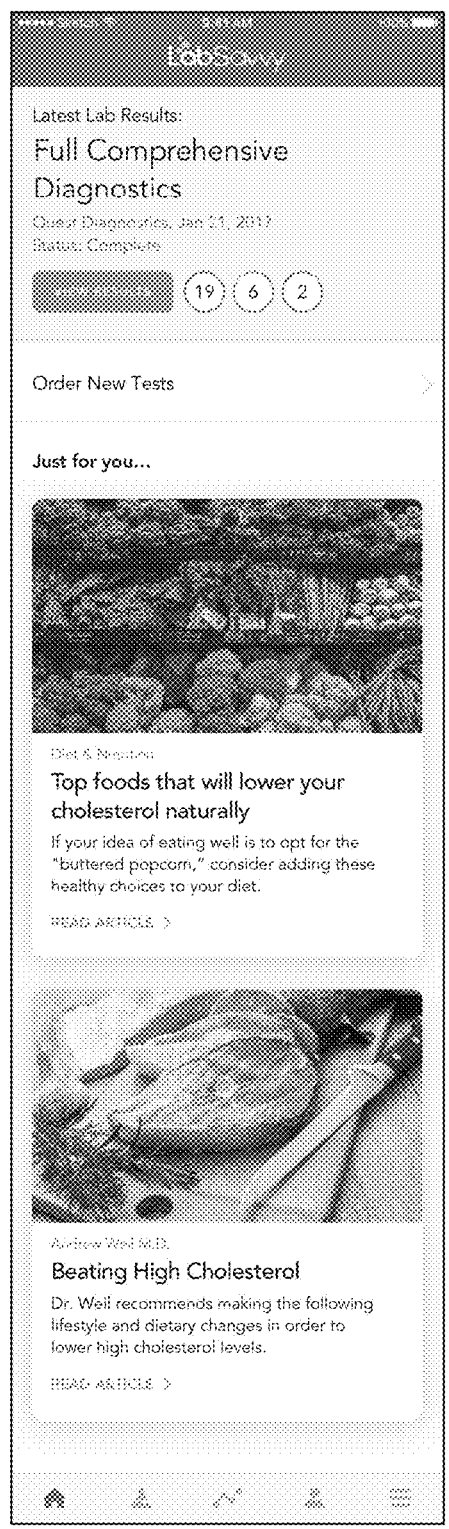
FIGS. 2A-2C are example screenshots of various user interfaces that may be provided through a lab test management system, such as the lab test management system illustrated in FIG. 1.

FIGS. 2A-6F are example screenshots of various user interfaces that may be provided through a lab test management system, such as the lab test management system 102 illustrated in FIG. 1. Referring first to FIGS. 2A-2C, screenshots of an example implementation of a patient user interface is provided. The patient user interface may be accessed by a patient using a smartphone, tablet, desktop or laptop computer (e.g., using a web browser) or any other similar computing device.

In general, a patient may log into the lab test management system 102 by providing appropriate credentials, which may include one or more of a user name, a password, a multi-factor authentication code, biometric information (e.g., a face scan or fingerprint), or any other similar identifying information. In one implementation, the patient may then be brought to a home or splash page customized for the patient. As illustrated in FIG. 2A, for example, the home page may include easy access to recent lab results and links to articles and other information relevant to the patient. In certain implementations, the articles and information presented to the user may be automatically selected and curated for the patient based on the patient's test history and results. Articles and educational information may also be selected for presentation to the patient based on one or more of the patient's preferences, selection by the patient's physician, characteristics of the patient (e.g., sex, age, ethnicity, etc.), or any other relevant factors.

Figure 2B:
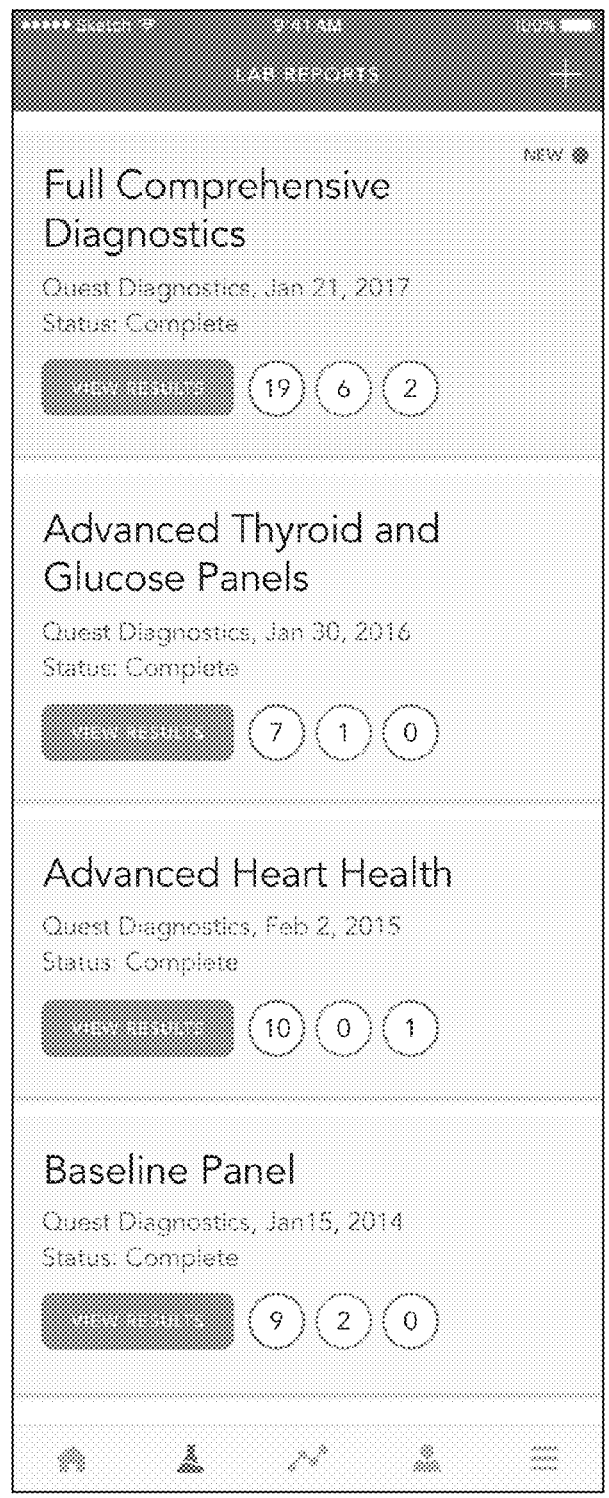

As illustrated in FIG. 2B, a patient may access his or her historical tests and lab reports through the user interface. Results may be arranged, for example, in reverse chronological order and the user may click or otherwise select any of the listed results to "drill-down" and receive additional information regarding a particular test. In certain implementations, each listed lab report may include indicators corresponding to the results of the corresponding tests. Such indicators may include, without limitation, color-coded shapes and/or numerical values that summarize the results to the patient in a clear and intuitive way.

Figure 2C:
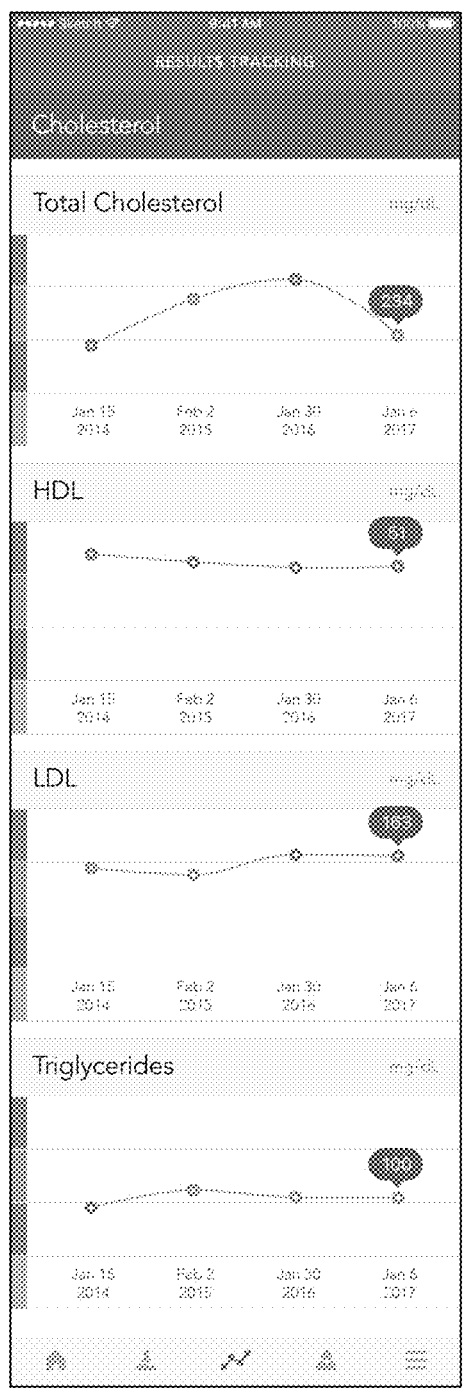

The user interface may also allow the patient to review historical trends in their health data. For example, FIG. 2C illustrates results from a series of cholesterol tests performed on the patient displayed in a series of line graphs. The line graphs of FIG. 2C are merely an example of a graphical representation of historical test results and it should be appreciated that a wide range of other representations may be used to convey information to a patient through the user interface.

Figure 3A:
FIGS. 3A-3B are example screenshots of various user interfaces that may be provided through a lab test management system, such as the lab test management system illustrated in FIG. 1, to facilitate access and retrieval of lab result information.
Figure 3B:
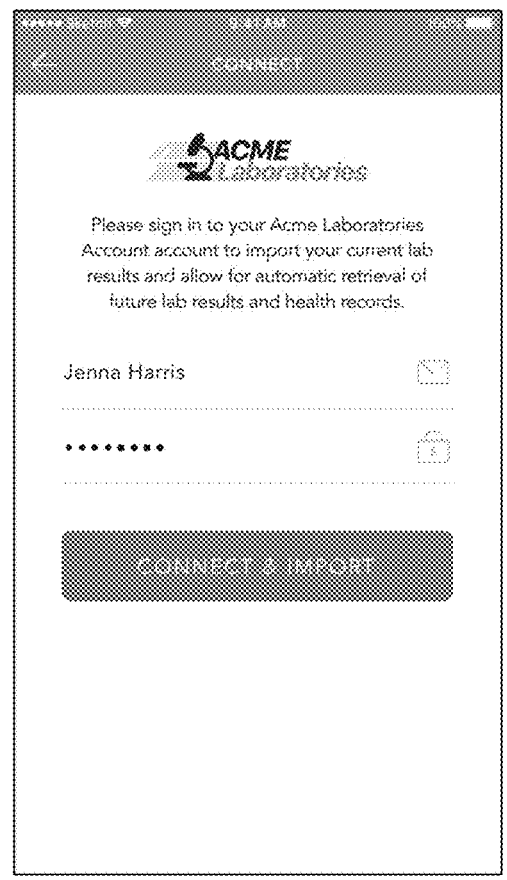

In certain implementations, a patient may also retrieve lab results through the user interface. For example, FIGS. 3A-3B are example screenshots of various user interfaces that may be provided through a lab test management system, such as the lab test management system 102 illustrated in FIG. 1 to facilitate access and retrieval of lab result information. As shown in FIG. 3A, the user may select from multiple test providers through the user interface to connect to and retrieve lab results and reports. As shown in FIG. 3B, in certain cases, such retrieval and importation may require secondary authentication or similar login information. Once logged in, lab results and reports for the patient may be automatically retrieved and imported into the lab test management system 102 for review and analysis by the patient.

Figures 4A, 4B:
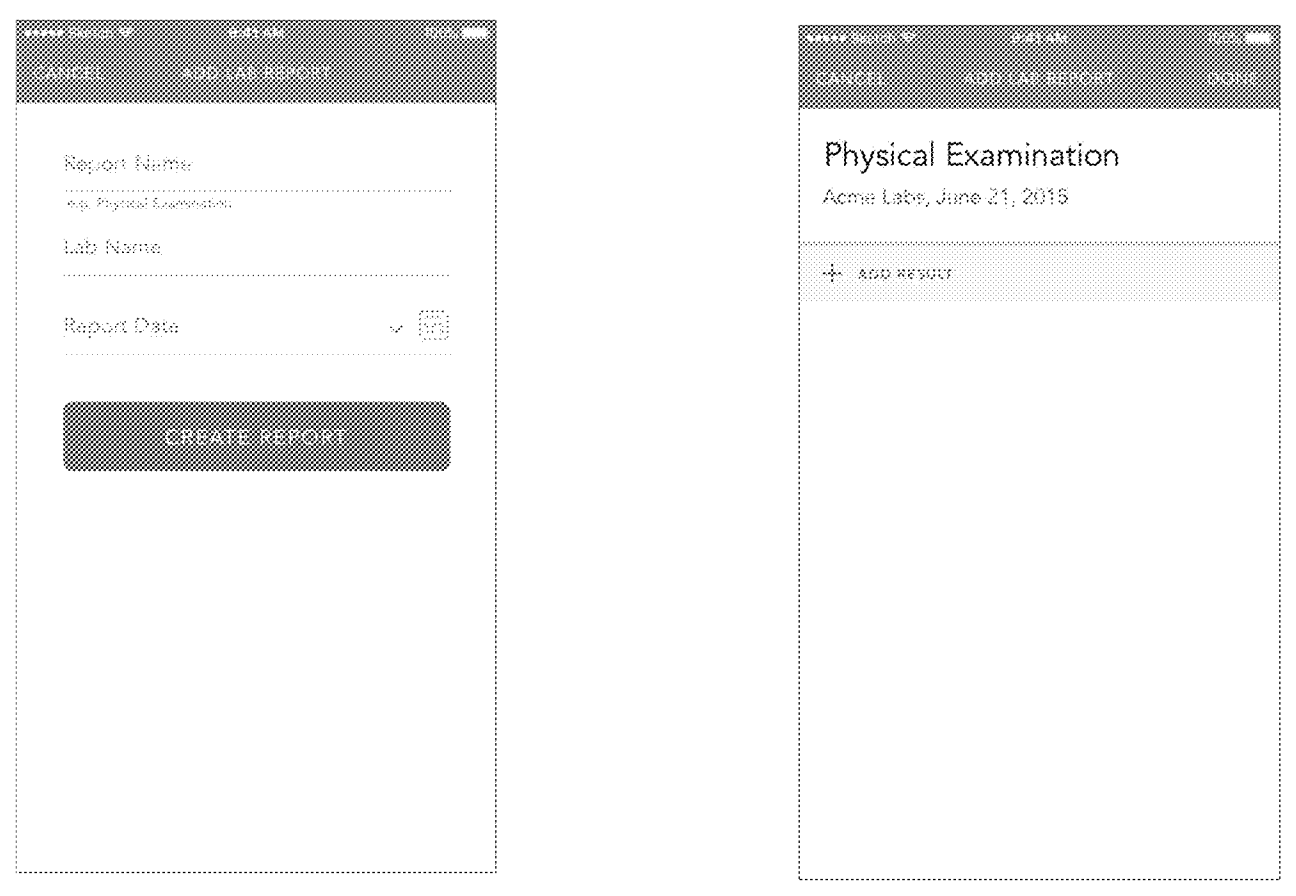
Figures 4C, 4D, 4E:
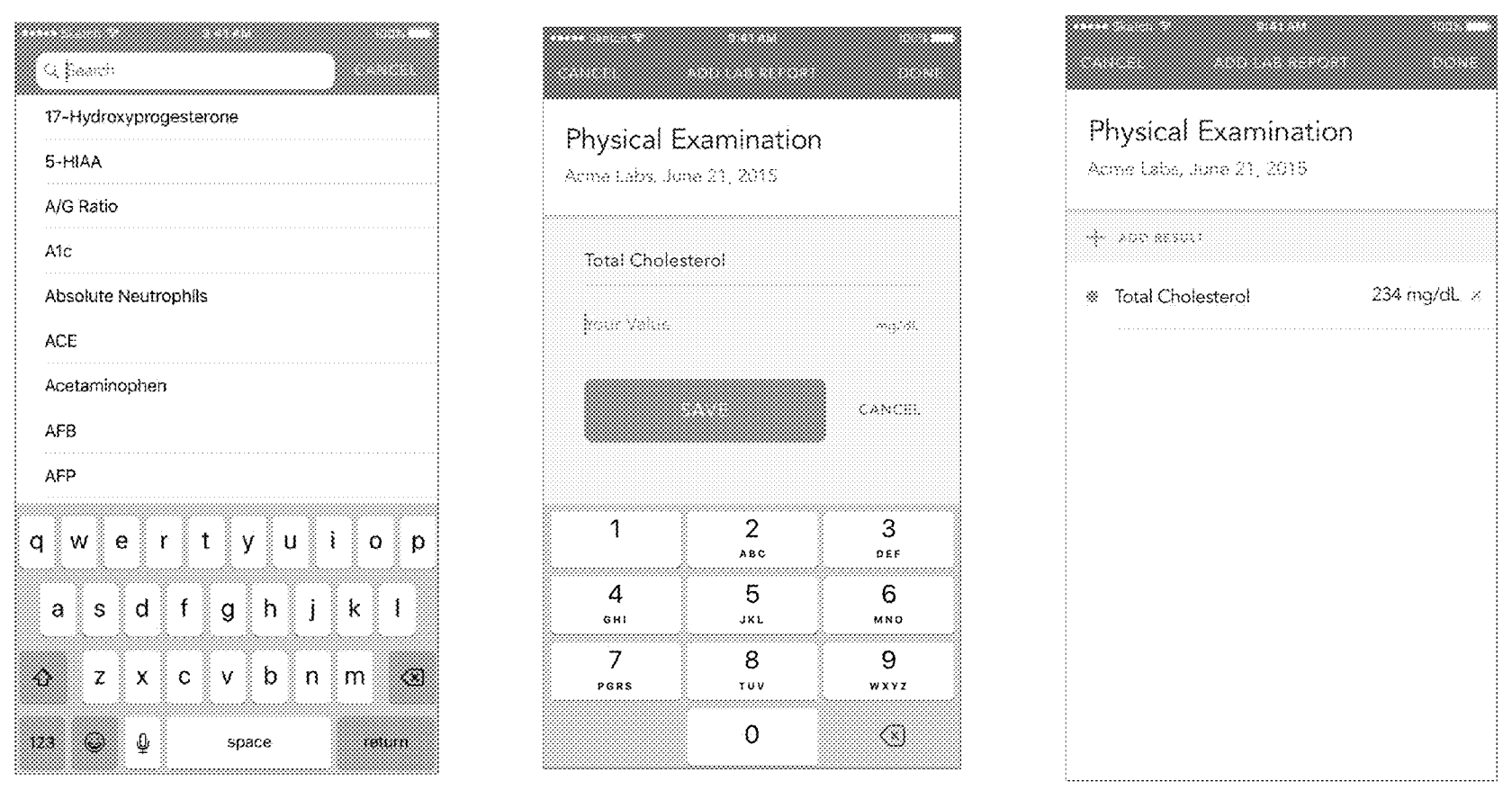
Figures 4E, 4F, 4G:
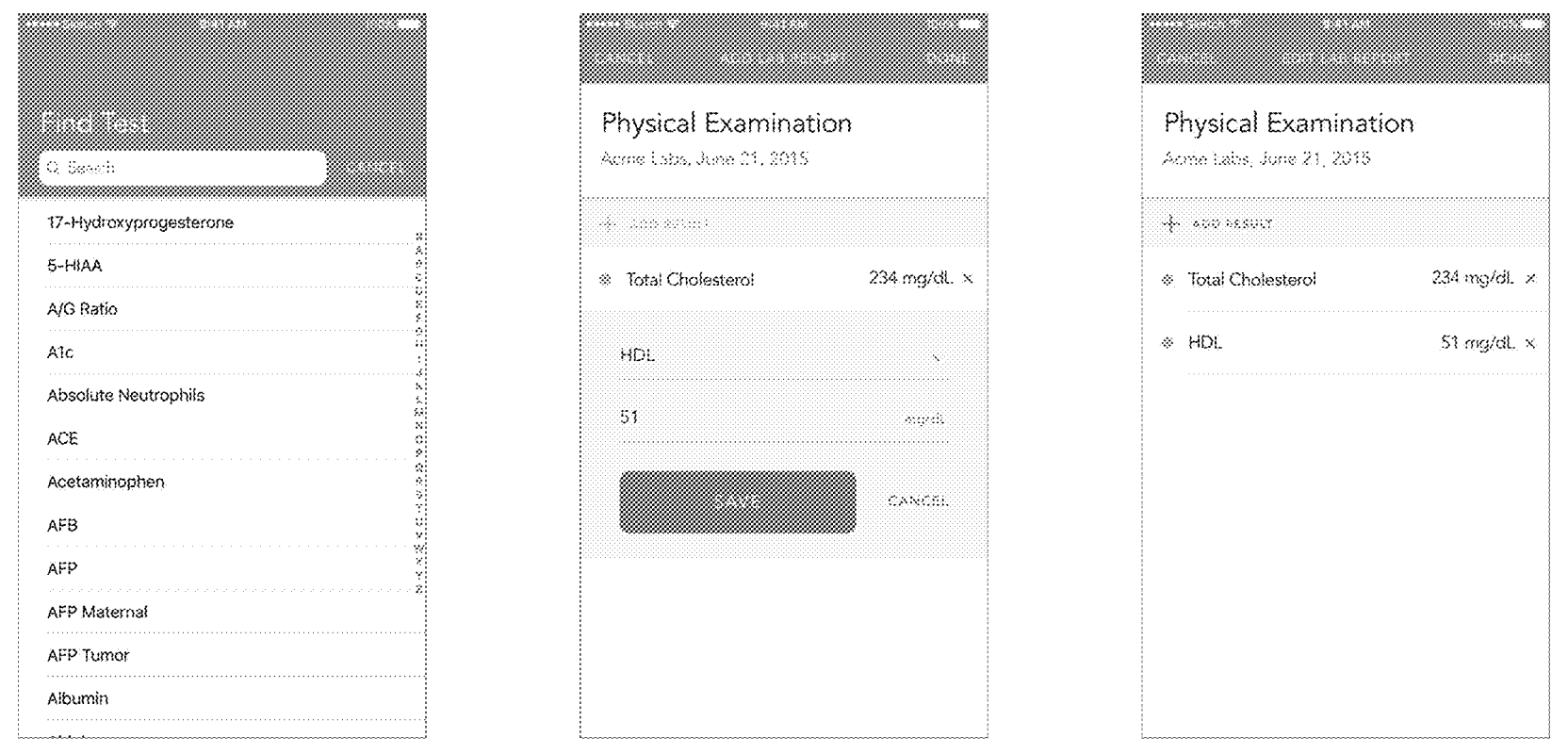
Figure 4H:
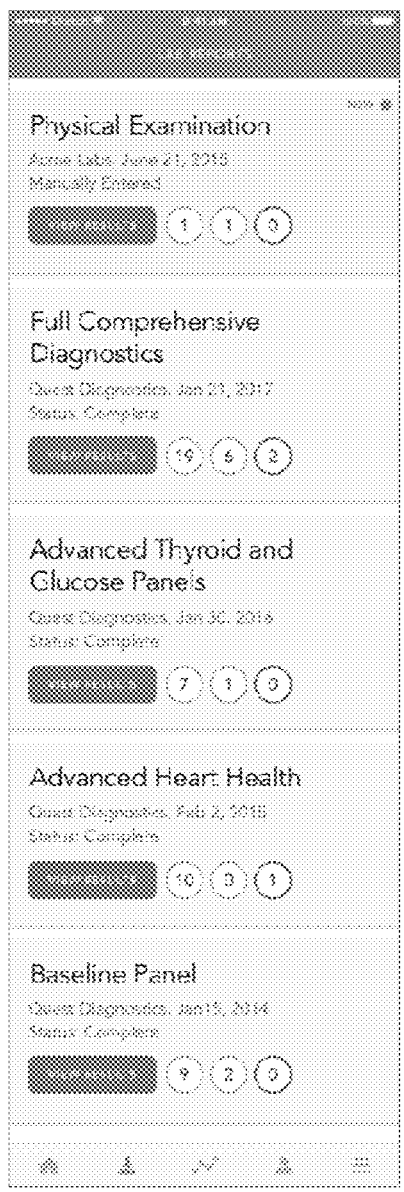
Figure 4I:
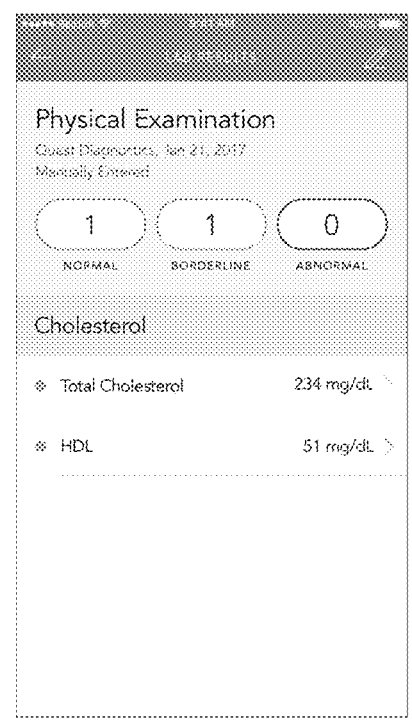

As an alternative to obtaining lab results from test providers, a patient may also manually generate and input lab results. An example process for manual input of lab results is illustrated in FIGS. 4A-4I. Beginning in FIG. 4A, the patient provides basic information creates a report by providing basic information for the report. Once created (as shown in FIG. 4B), the user may then add specific results to the report. For example, in FIGS. 4C-4E, the patient finds a total cholesterol test in a searchable list of tests, provides the corresponding test results for the test, and adds the test to the previously created report. The patient then performs a similar process to add results for an HDL test, as illustrated in FIGS. 4E-4G. Once completed, the resulting report is made available to the patient in the list of available lab reports (shown in FIG. 4H) and may be selected to obtain further information, such as general overview and analysis of the test results, such as shown in FIG. 4I.

FIGS. 5A-5G illustrate example user interfaces for ordering lab test using a system, such as the lab test management system 102 of FIG. 1. In contrast to the user interface illustrated in FIGS. 4A-4I, which was generally available to a patient user of the system 102, the user interface illustrated in FIGS. 5A-5G may be made available to a clinical practitioner, lab technician, or other healthcare practitioner involved in procuring, performing, reporting, or otherwise administering test for a patient.

Figure 5A:
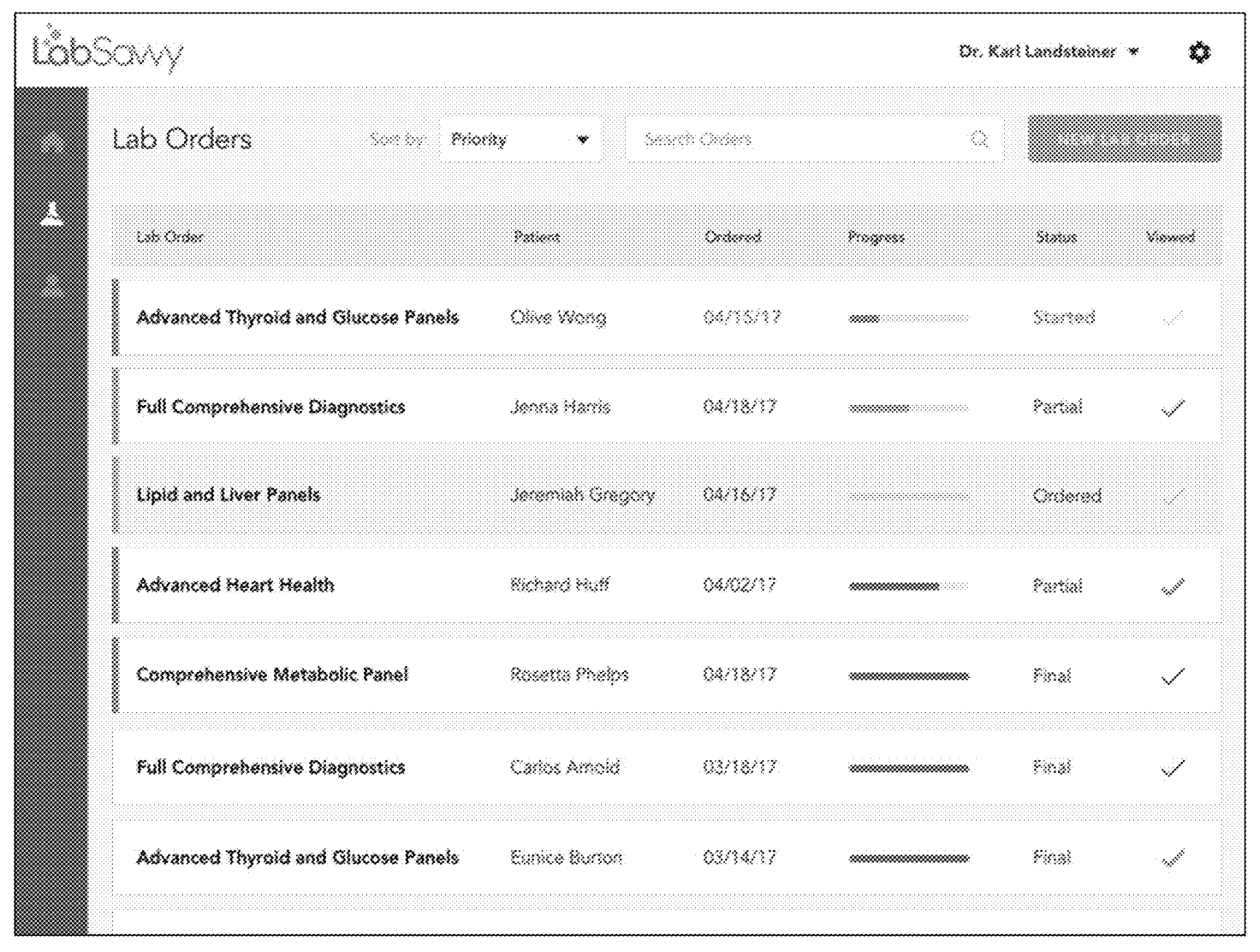

As shown in FIG. 5A, a user of the system 102 may be presented with a searchable and sortable list of tests/panels managed by the system 102. The list may include various pieces of information regarding the tests/panels including, without limitation, a patient name, a date the test/panel was ordered, current progress, and current status of the test.

Figure 5B:
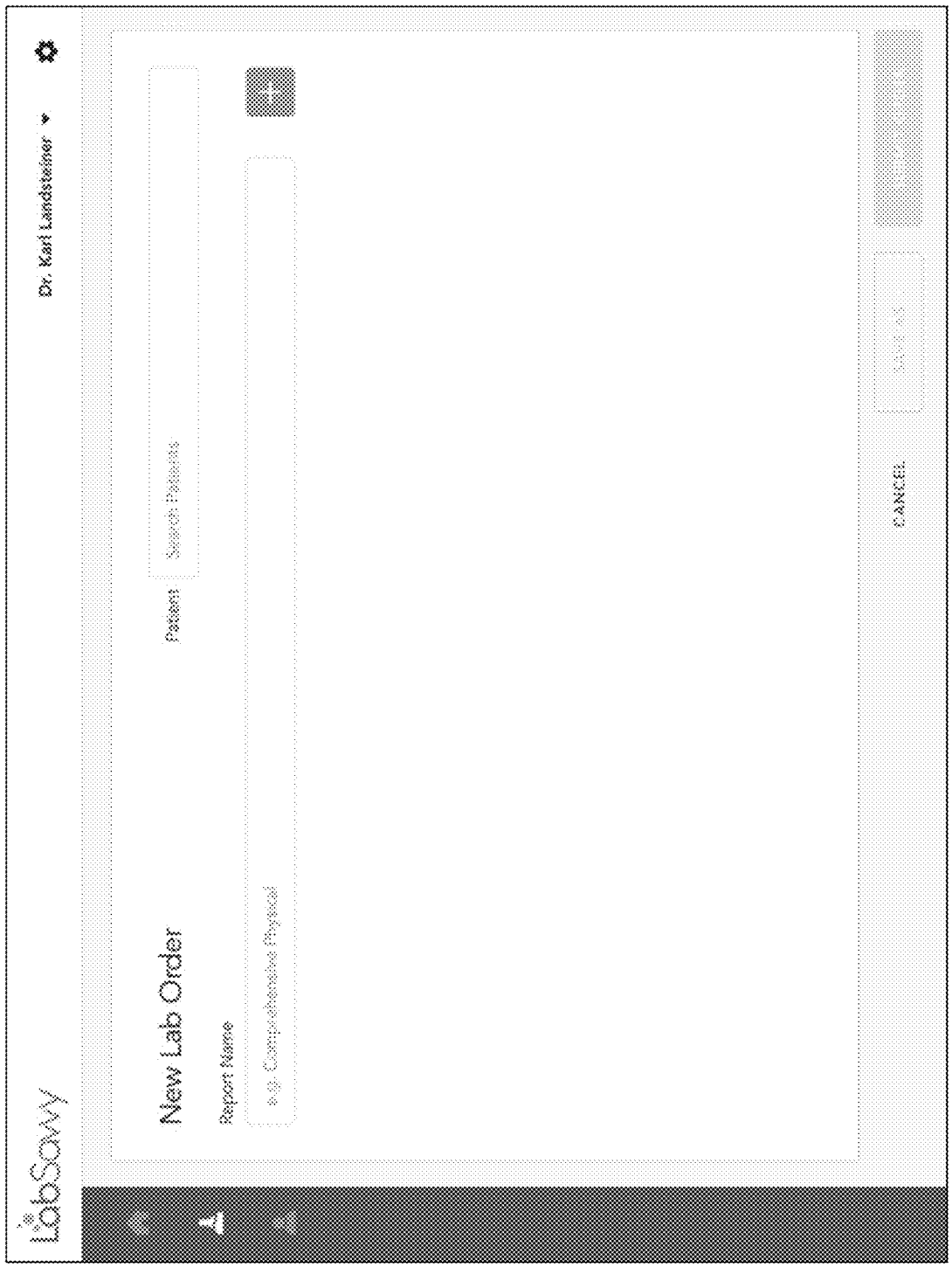
Figure 5C:
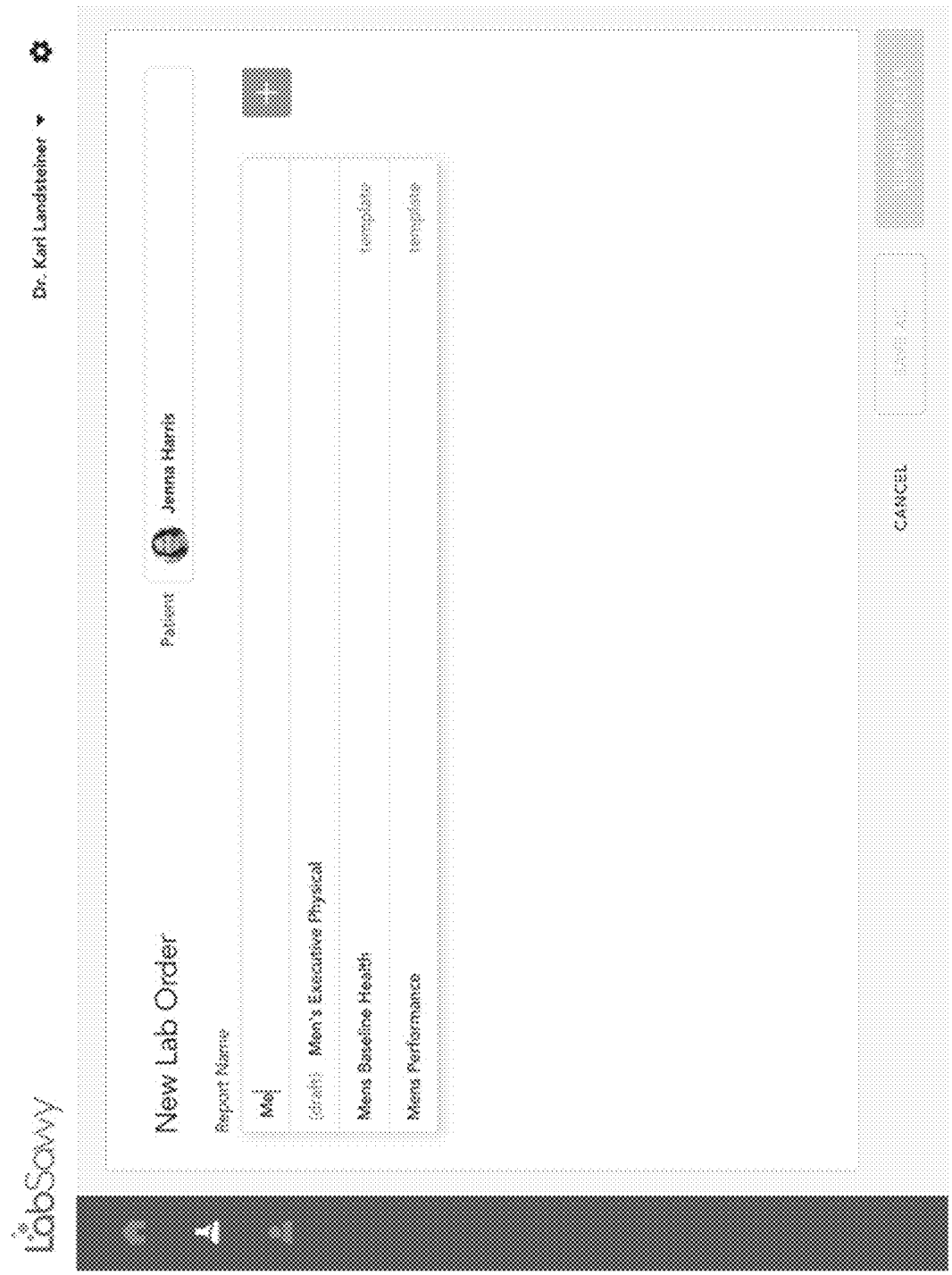
Figure 5D:
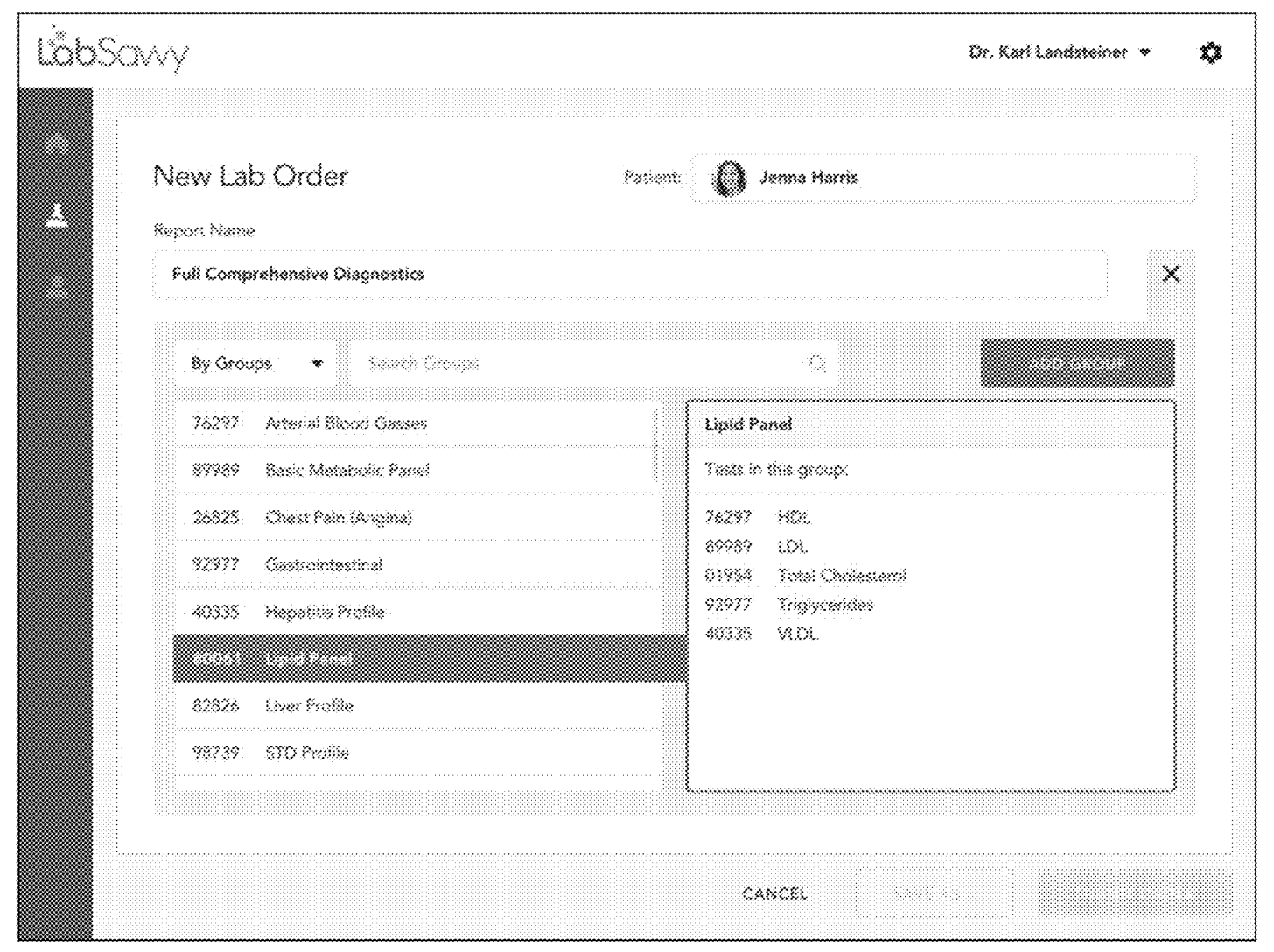
Figure 5E:
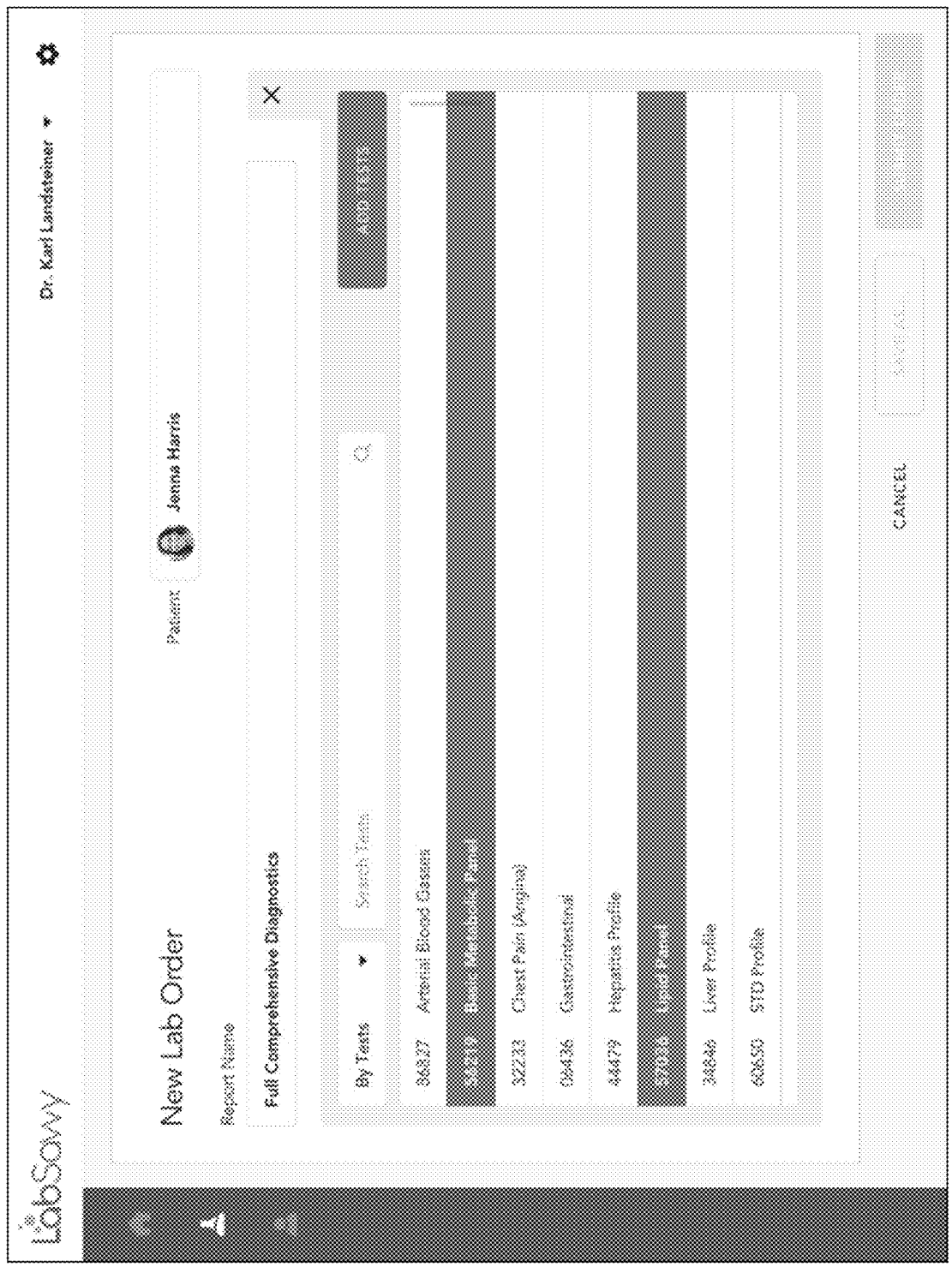
Figure 5F:
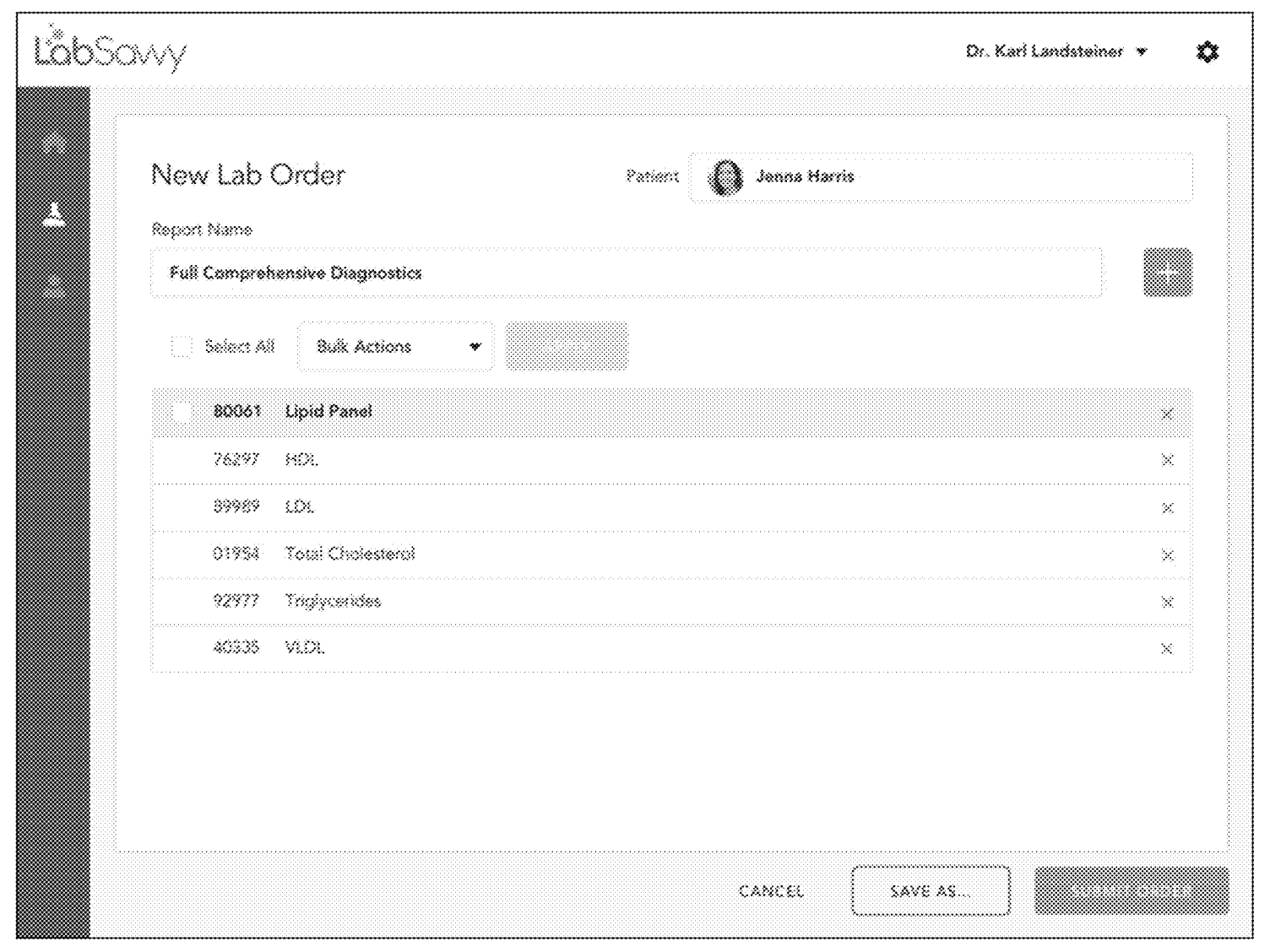
Figure 5G:
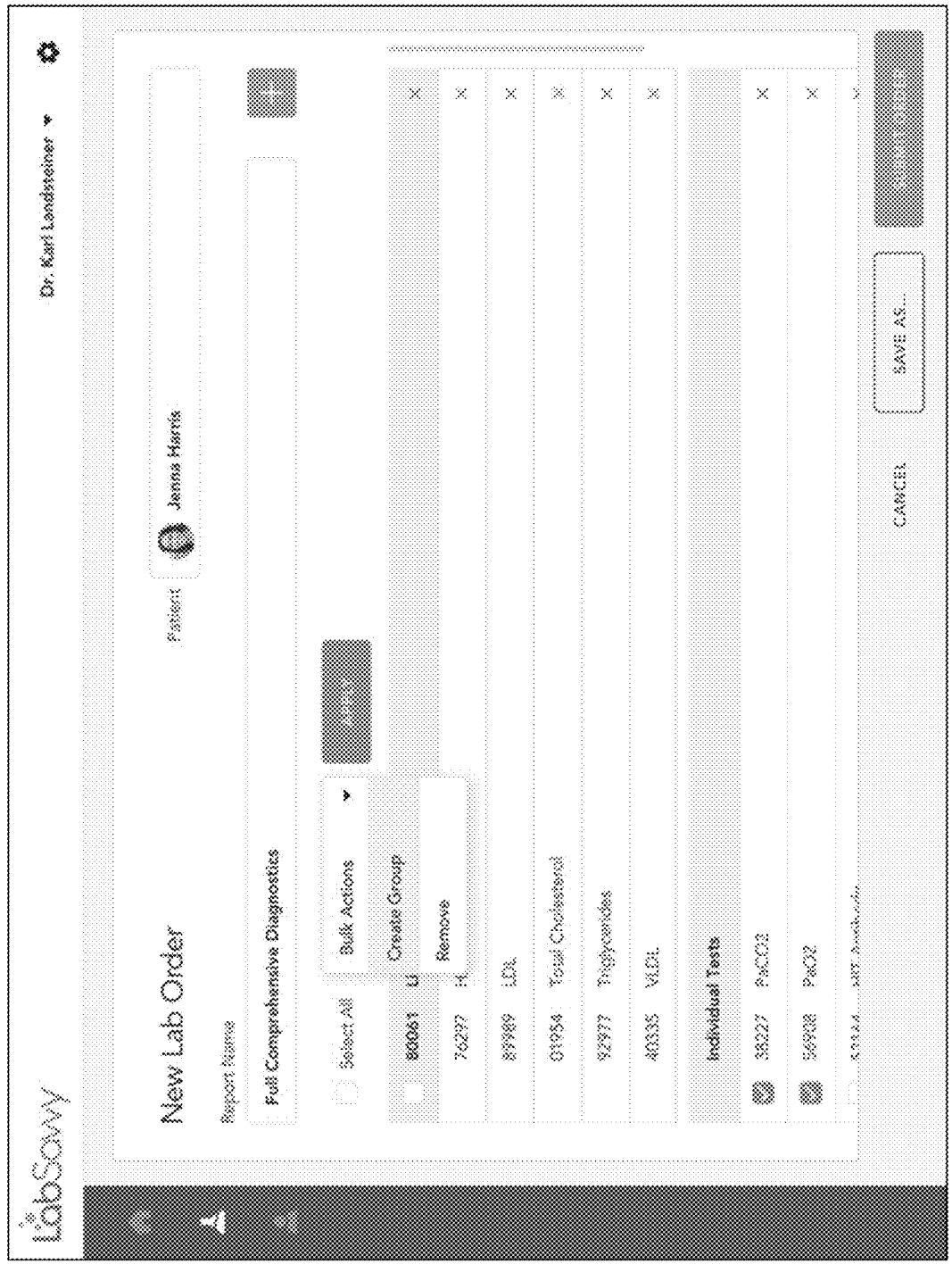

Referring to FIG. 5B, the system 102 allows healthcare practitioners to generate and submit new lab orders. In certain implementations, such ordering may include identifying a patient and providing a name for the lab being ordered, as shown in FIG. 5C. The healthcare practitioner may then select one or more tests to be performed as part of the order. When doing so, the practitioner may be presented with and select from a searchable list of test groups, each of which may include one or more individual tests (as shown in FIGS. 5D-5E). The practitioner may add the test group as a whole to the order or may drill down into a given group to select individual tests. As illustrated in FIGS. 5F and 5G, the practitioner may also create, edit, or otherwise modify test groups, thereby enabling greater customization of lab orders.

FIGS. 6A-6F illustrate another example user interface that may be implemented using a system in accordance with the present disclosure, such as the lab test management system 102 of FIG. 1. More specifically, the user interface of FIGS. 6A-6F illustrates how an implementation of the system may facilitate management of patient information and test results.

Figure 6A:
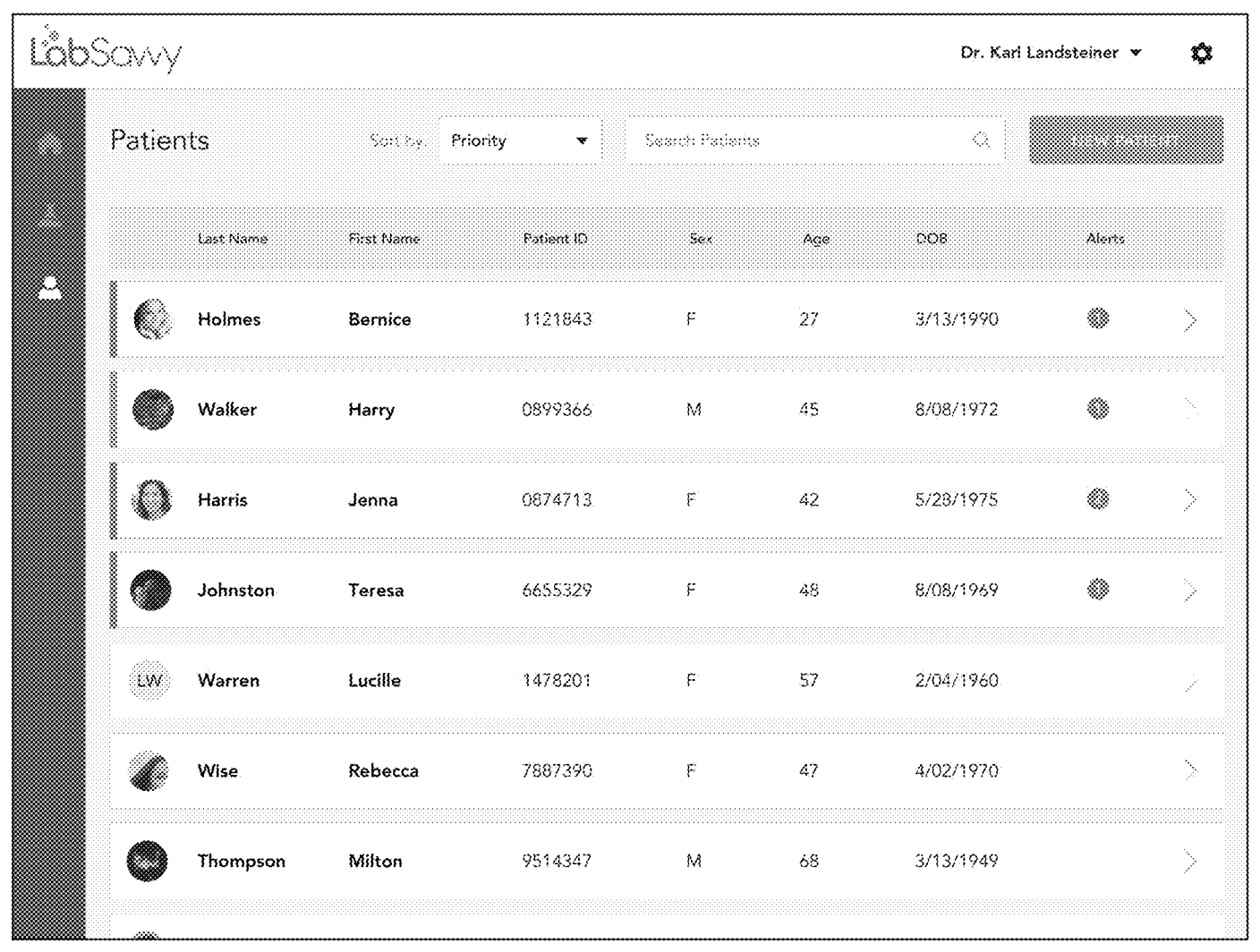

As shown in FIG. 6A, the user interface may present a list of patients to the user along with basic information (e.g., patient ID, sex, age, date of birth) for each patient. In addition to this basic information, the list may also include an indicator for alerts associated with each patient. For example, such an indicator may be used to indicate, among other things, new test results received for a patient, new communication received from or relating to the patient, a test that is required and due, and the like.

Figure 6B:
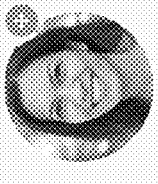
Figure 6C:
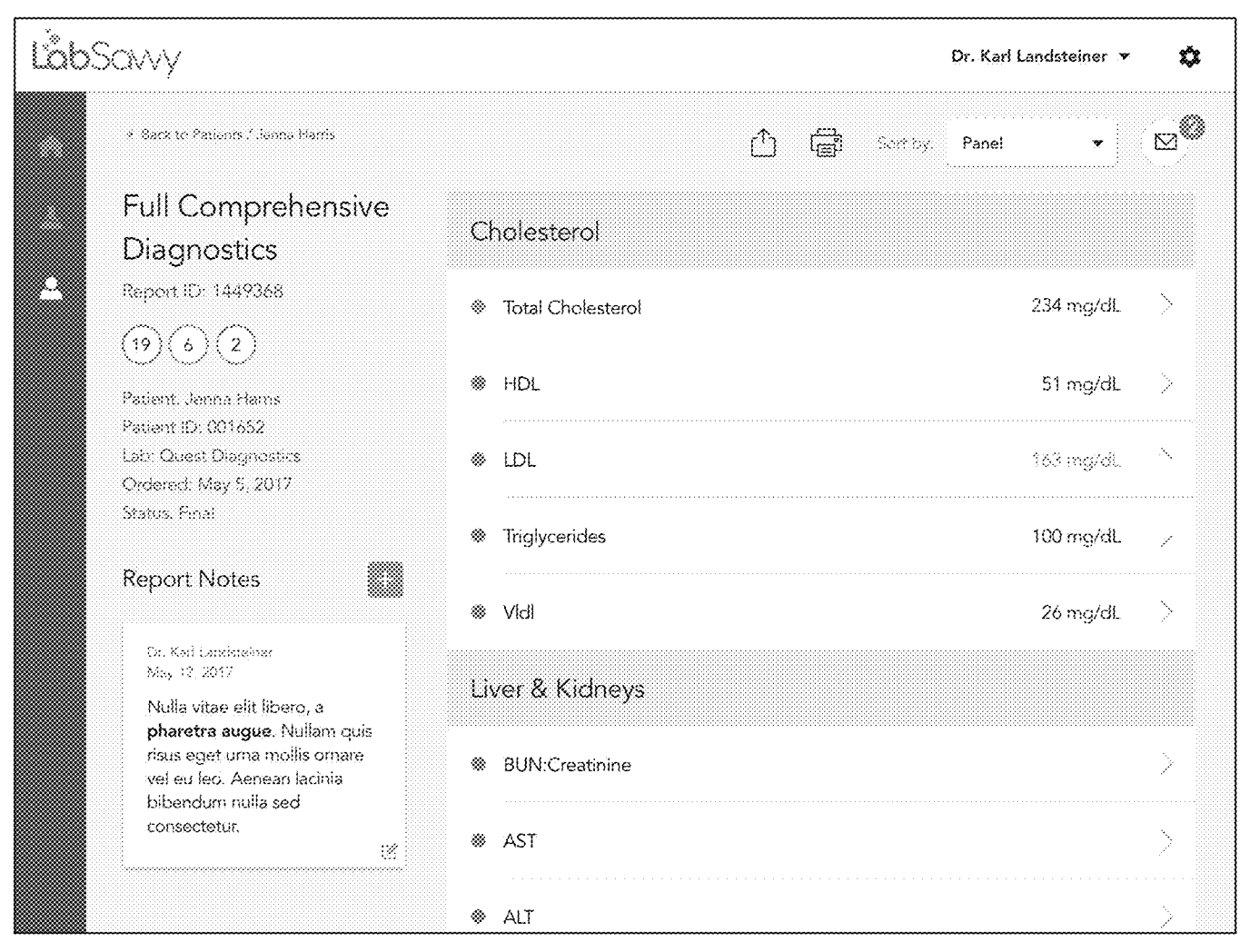
Figure 6D:
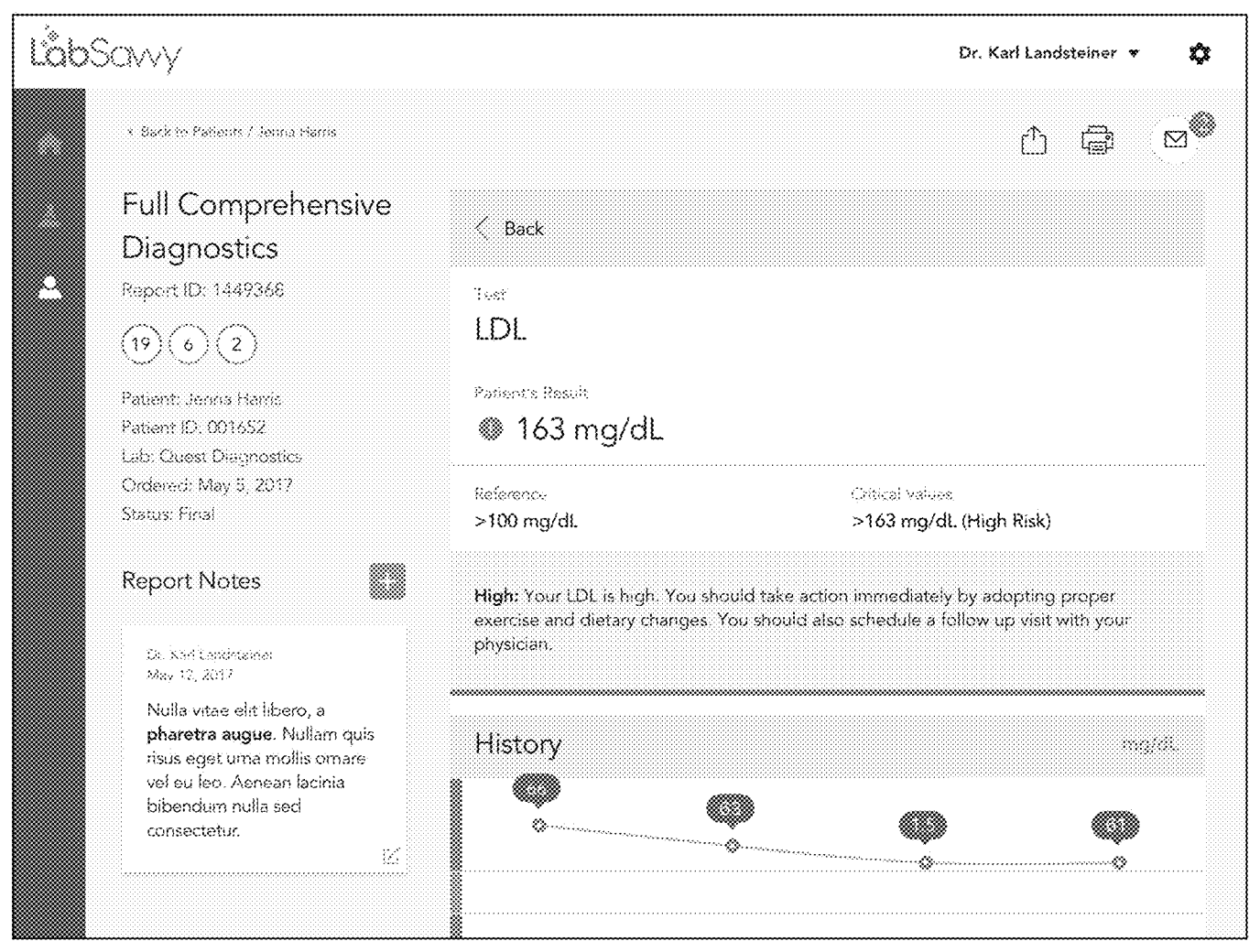

The user may click or otherwise select a patient and be presented with further details, such as illustrated in FIG. 6B. For example, in certain implementations, each patient may have a patient profile that includes basic biographical information of the patient, a list of recent lab reports, and a list of patient notes, which may be made private and not visible to a patient. As shown in FIG. 6C, the practitioner may select one of the reports listed on the patient profile page and be presented with summary information regarding the selected report. Each individual test within the report may further be selected to provide specific information regarding the results of the individual test, as shown in FIG. 6D. In certain implementations, test results may be supplemented with historical information and data regarding the patient such that trends regarding the test outcome may be readily identified. For example, FIG. 6D includes LDL test results and is supplemented with a line graph including previously obtained LDL test results, which indicate an overall downward trend.

Figure 6E:
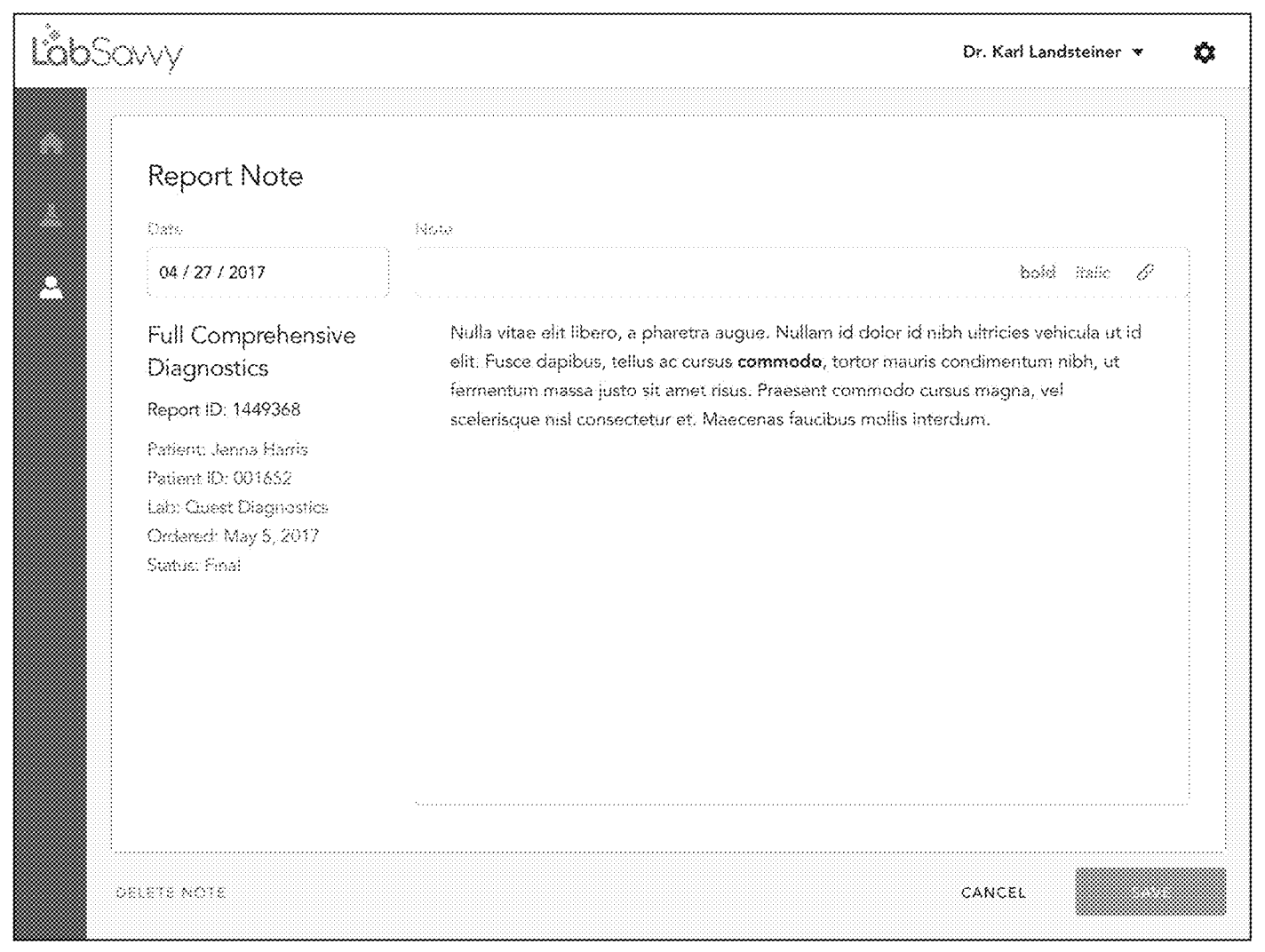

FIG. 6E illustrates a portion of the user interface for inputting report notes which may be appended to specific lab reports. As previously noted, notes may be made private such that the patient is unable to view them. In certain implementations, permission to view some or all notes associated with a report may be modified by an authorized user. Alternatively or in addition to setting such permission, users may belong to particular groups or organizations with permission to view notes.

As previously discussed in the context of FIG. 2C, implementations of the present disclosure may include charting functions for displaying test result data to a user. As shown in FIG. 2C, for example, a patient user interface in accordance with the present disclosure may allow a user to access and view consolidated historical test result data for a variety of tests in an intuitive and user-friendly format.

Figure 7:
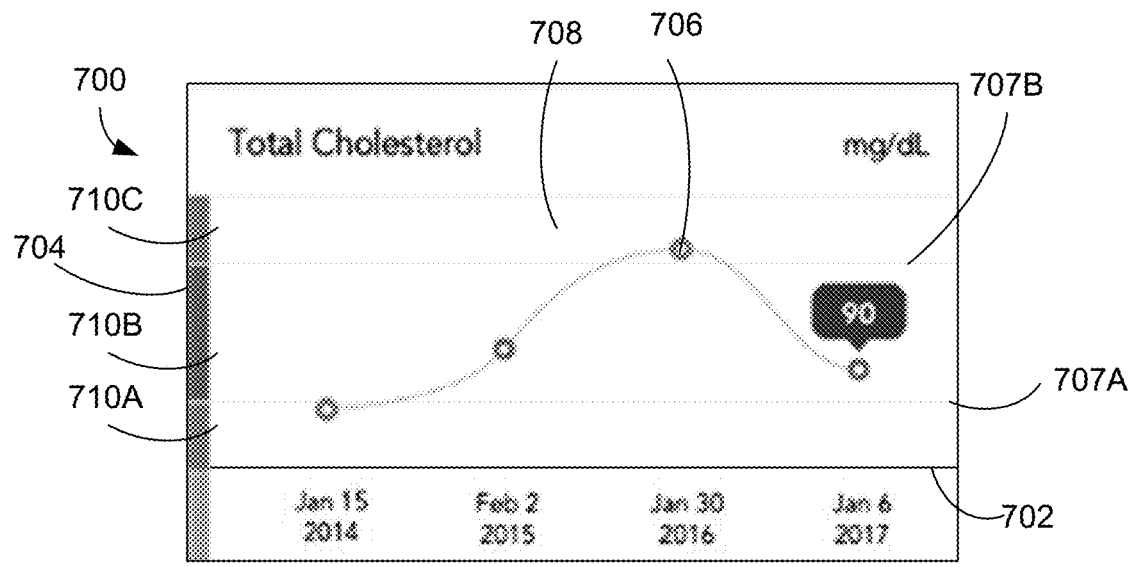
FIG. 7 is a first example chart which may be generated using systems and methods of the present disclosure, the chart including three visually delineated bands.

FIG. 7 is an example chart 700 illustrating historical test result data that may be generated and displayed in implementations of the present disclosure. As shown in FIG. 7, the chart 700 may include a horizontal axis 702 corresponding to time and a vertical axis 704 corresponding to test result values. The chart 700 may further include indicators (e.g., indicator 706) disposed within a display area 708 of the chart 700, with each indicator corresponding to a test result value obtained on a given date.

The chart 700 may also include one or more visually delineated ranges for facilitating interpretation of the illustrated test data. For example, the chart 700 includes has a total chart range divided by two thresholds 707A, 707B such that the display area 708 is divided into three bands 710A-710C. More specifically, the display area 708 is divided into a first band 710A corresponding to a first range of test values (e.g., a low test value range), a second band 710B corresponding to a second range (e.g., a middle or "normal" test value range), and a third band 710C corresponding to a third range (e.g., a high test value range). Accordingly, by plotting test result values in the display area 708, a user can readily read and interpret their historical test result data and identify any trends within such data.

Figure 8:
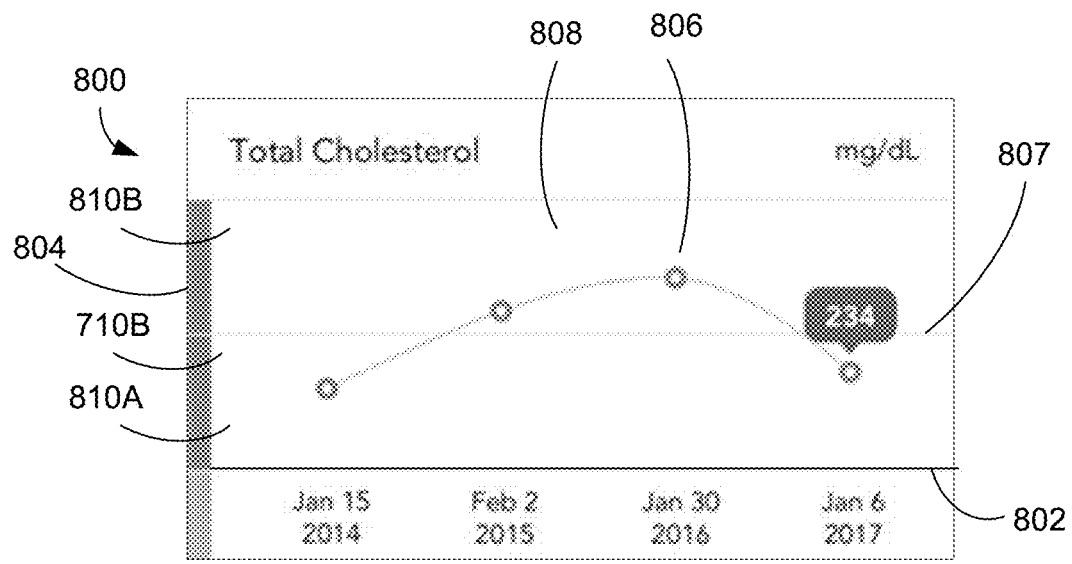
FIG. 8 is a second example chart which may be generated using systems and methods of the present disclosure, the chart including two visually delineated bands.

FIG. 8 is a second example chart 800 for illustrating historical test data that may be generated and displayed in implementations of the present disclosure. Similar to the chart 700 of FIG. 7, the chart 800 includes a horizontal axis 802 corresponding to time and a vertical axis 804 corresponding to test result values such that indicators (e.g., indicator 806) within a display area 808 of the chart 800 indicate a test result value obtained on a given date.

In contrast to the chart 700, which included multiple thresholds, the chart 800 includes only a single threshold 807. Accordingly, the chart 800 includes only two bands 810A, 810B. In certain implementations, the threshold 808 may delineate low and normal test result values such that the first band 810A corresponds to a low range of the test results and the second band 810B corresponds to a normal range of the test results. In other implementations, the threshold 808 may delineate normal and high test result values such that the first band 810A corresponds to a normal range for the test result values and the second band 810B corresponds to a high range of the test result values.

While illustrating historical test results values over time in a graphical format is an intuitive approach for analyzing a patient's or one's own health, problems can arise when including interpretive aids, such as the bands 710A-710C and 810A, 810B, due to possible inconsistencies in the underlying test result data. In particular, each test performed for a given test type may define test ranges differently. For example, a first original equipment manufacturer (OEM) of testing equipment may calibrate its devices such that a range of 50-70 units for a given test type is defined as "normal". Meanwhile, a second OEM of testing equipment may calibrate its devices such that a range of 55-65 units for a given test type is considered "normal". Similarly, test ranges for a given piece of testing equipment may be redefined or updated over time such that the test ranges are defined differently depending on when a test is conducted. For example, an OEM may update the ranges or thresholds for a given test in response to further medical research regarding the particular parameter measured using the test or similar developments. So, referring back to the chart 700 of FIG. 7, the width and/or offset of the middle band 710B indicating a normal test outcome may vary between tests. Such inconsistencies may lead to confusion and/or misinterpretation of test results by patients or physicians and generally complicates the presentation of historical test result data.

To address the foregoing issues, among others, implementations of the present disclosure include an improved approach to generating and displaying historical test results such that test result data and associated trends in test result data are easier to identify and interpret. In particular, the systems and methods in accordance with this disclosure generate and display charts for which potentially disparate or inconsistent test ranges are normalized. To do so, the approaches disclosed herein leverage the fact that test result data received from testing equipment, laboratories, etc. generally includes both a test result value (e.g., a raw test result value) as well as a test range defining a normal or healthy range of values for the given test. Notably, such test range data is provided for each test result and is therefore associated with the specific piece of equipment on which the testing was conducted and reflects configuration of the equipment at the time the test was conducted.

The normalization process described herein generally includes fitting historical test result data for multiple tests of a particular test type to a common chart. The chart generally includes a total range for which a chart subrange, such as a "normal" subrange, is specified. For example, in one specific non-limiting example, the total range of a chart may be 100 units and extend from 0 to 100 units and a chart subrange corresponding to a normal test result may be defined as 20 units and extend from 50-70 units. Each test result value of the historical test data is then fit to the chart based on correlating the test range for the specific test result to the chart subrange. For example, a first test result may include a test result value of 55 and have a test range of 30 units from 45-75 while a second test result may also include a test result value of 55, but may have a test range of 10 units from 50-60 units. The location of indicators corresponding to each of the test result value is then determined by fitting the test ranges to the chart subrange. In other words, each test result value is displayed within the total range of the chart by scaling and offsetting the test range of the test result to the chart subrange.

Using the foregoing values, for instance, fitting the first test result and identifying the location of a first indicator corresponding to the first test result value would generally involve both scaling and application of an offset. More specifically, scaling would be required to account for the difference in the test range (30 units) and that of the chart subrange (20 units) while offsetting would be required to account for the fact that the test range is centered about 50 units while the predefined range of the chart is centered about 60 units. As a result of such fitting, the raw test value of 55 units would translate to approximately 57 units relative to the total range of the chart. The second test result would similarly require each of scaling and offsetting and would result in placement of a second indicator at 60 units relative to the total range of the chart.

Using the foregoing approach, regardless of the specific manipulation applied to each test result of the historical test result data, the indicator corresponding to the test result is placed in the chart in a manner that indicates the corresponding test result value's relative relationship to a particular test result interpretation, e.g., a normal test result. Accordingly, a user (e.g., a patient or physician) can readily determine and interpret historical test result data without the confusion associated with inconsistent, changing, or otherwise variable test ranges.

In certain implementations of the present disclosure, additional features of the chart may also be implemented to improve the visual presentation and/or utility of the charts. For example, charts may include margins for visually separating chart elements, colored bands (or similar visual indicators) for delineating different ranges (e.g., a low range, a normal range, and a high range), and numerical values corresponding to one or more of the displayed indicators. In other implementations, a user may be able to click on or otherwise select various elements of the chart to access additional information. For example, in response to selecting a particular indicator, the user may be presented with detailed test result information, such as the specific raw test result value for the indicator and the specific test range for the corresponding test. Selecting an indicator or other element of the chart (e.g., a band corresponding to a particular interpretation) may also provide the user with educational content, such as articles, text, video, audio, or other multimedia, related to the test type, the user's results, recommendations for the user, and the like.

Figure 9A:
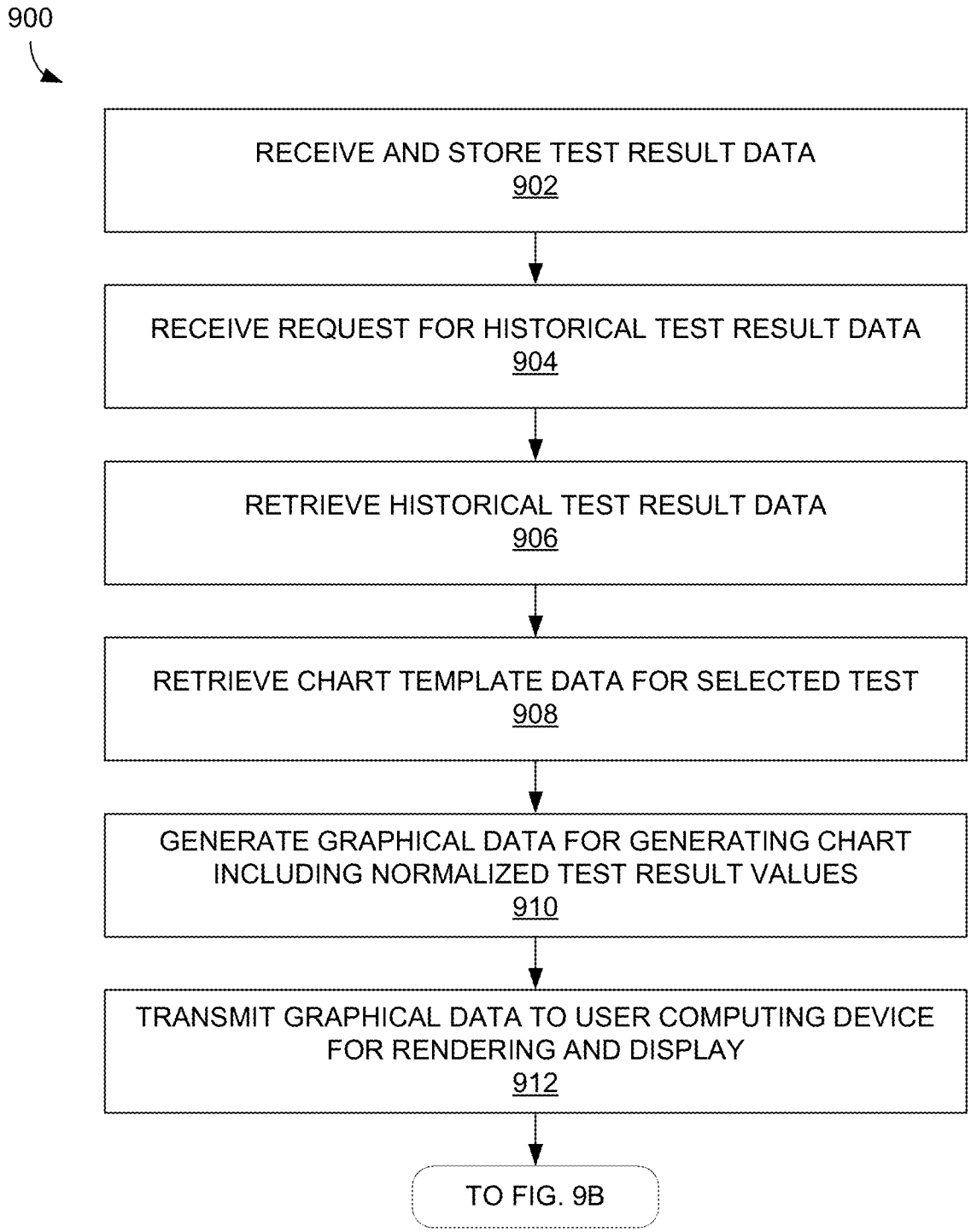
FIGS. 9A-9B are flow charts illustrating a method for generating and providing graphical data for generating charts according to the present disclosure.
Figure 9B:
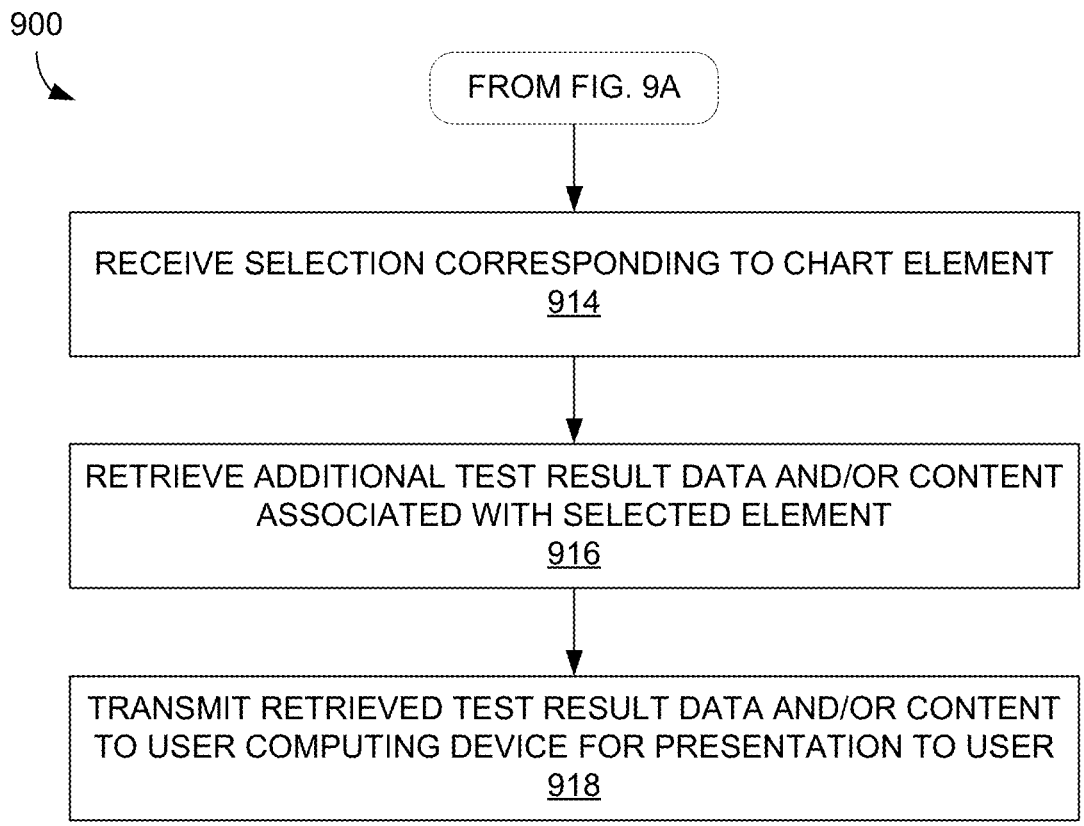
Figure 10:
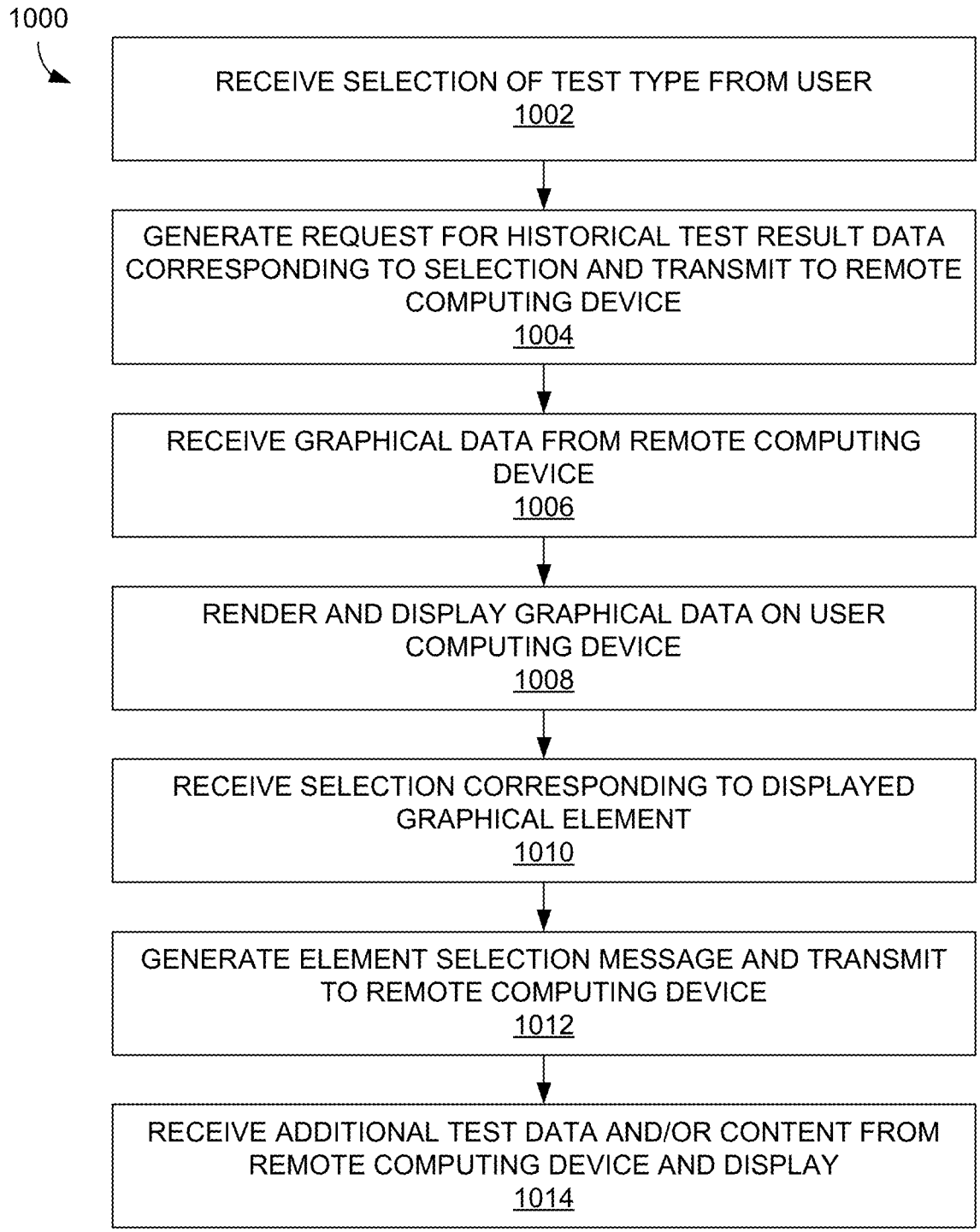
FIG. 10 is a flow chart illustrating a method for requesting and displaying graphical data according to the present disclosure.

The foregoing and other aspects of the present disclosure will now be discussed in further detail with reference made to the figures. FIGS. 9A, 9B, and 10 are flow charts illustrating respective methods 900, 1000 related to generation, request, and display of the historical chart illustrated in FIG. 11D. More specifically, FIGS. 9A and 9B illustrate a first method 900 directed to generating graphical data corresponding to historical test results for rendering and display on a computing device. The first method 900 may be executed, for example, by a server or similar central computing system (e.g., the lab test management system 102 of FIG. 1) to generate charts (such as that illustrated in FIG. 11D) for display on a user computing device (e.g., the user computing device 122 of FIG. 1). FIG. 10, on the other hand illustrates a second method 1000 directed to requesting, receiving, and displaying graphical data for rendering and display at a user computing device. The second method 1000 may be executed, for example, by a user computing device, such as the user computing device 122 of FIG. 1, to request graphical data that is then rendered and displayed as charts, such as that included in FIG. 11. Each of the first method 900 and the second method 1000 further include additional steps directed to the request and provision of reporting and/or educational content that extend beyond steps directed to generating and displaying the historical test result data.

For purposes of the following example implementation and to provide context, reference is made to the various system elements of the lab result processing system 100 of FIG. 1. For example, the first method 900 will generally be described as being executed by the lab test management system 102 of FIG. 1 while the second method 1000 will generally be described as being executed by the user device 122 of FIG. 1. It should be appreciated, however, that any reference to elements of the lab result processing system 100 of FIG. 1 should be regarded as examples only and implementations of the present disclosure are not necessarily limited to the specific elements, architecture, etc. of the system 100 of FIG. 1.

Referring first to the method 900 of FIG. 9, the lab test management system 102 receives lab test result data. As previously described in the context of FIG. 1, the lab test management system 102 may receive lab test result data from one or more lab/clinician systems (e.g., systems 104-110 of FIG. 1) subsequent to a user or patient being tested. Due to discrepancies in data formats and communication protocols, receipt of the lab test result data in operation 902 may include passing the lab test result data through a translation layer 112 to standardize the lab test result data prior to storage (e.g., in the lab test result data store 116 of FIG. 1).

The specific information included in the lab test result data and received by the lab test management system 102 may vary based on the type of test conducted; however, in general, for a given test for which lab test result data is received, the lab test result data includes at least a test result value corresponding to the result of the test and a test range for interpreting the test result value. In many cases, for example, the test range identifies "normal" or "healthy" values for the test. Notably, while the following description focuses primarily on ranges corresponding to normal or healthy results, the present disclosure should not be regarded as being limited to such implementations. Rather, implementations of the present disclosure may rely on any range provided with the test result data for purposes of interpreting the test result values.

As previously noted, the test range for any two tests may vary despite the tests being of the same test type. For example, in certain cases, original equipment manufacturers (OEMs) may define normal test ranges differently such that normal test ranges for a first test conducted on a first OEM's machine may differ from those of a second test conducted on a second OEM's machine. In other cases, two pieces of testing equipment of the same type or model may be calibrated to have different test ranges. In still other cases, test ranges may be updated or modified over time in light of new research, etc. Accordingly, interpretation of test result values generally requires that both the test result value and the test range for the specific test be provided.

Additional information in the test result data may include, without limitation, a date or time stamp indicating when the test was performed and/or when a tested sample was obtained, a patient identifier, a lab/clinic identifier, an identifier associated with manufacturer of the testing equipment, a flag or identifier for the type of test conducted, an identifier (e.g., a serial number) of the specific piece of testing equipment on which the test was conducted, and the like.

Subsequent to collecting test result data, the lab test management system 102 may receive a request for historical test result data (operation 904). In certain implementations, the request may be generated by and transmitted to the lab test management system 102 by the user computing device 122 in response to the user selecting a particular test or navigating to a test result page of a user interface executed on the user computing device 122. For example, in one implementation, the user may be presented with a list of test types for which historical test result data is available and the request may then be transmitted to the lab test management system 102. In another implementation, one or more requests may be automatically generated and transmitted by the user computing device 122 in response to the user navigating to a test result page or section of the user interface. For example, FIG. 2C illustrates a "Results Tracking" page of the interface including multiple charts of historical test result information. Accordingly, the user computing device 122 may generate and transmit one or more requests to lab test management system 102 in response to the user navigating to the "Results Tracking" page.

The request received by the lab test management system 102 may include, among other things, one or more of an identifier of the patient in question and an identifier corresponding to the particular test type for which results are to be retrieved. The patient in question may be the user themselves or may be a patient of the user (e.g., in implementations in which a physician or other medical professional is able to access lab test results). More generally; however, the request includes sufficient information for the lab test management system 102 to identify historical test result data for a given test type associated with a particular patient.

In response to receiving the request and based on the contents of the request, the lab test management system 102 retrieves the relevant historical test result data corresponding to the request (operation 906). More specifically, for one or more tests of the test type associated with the request, the lab test management system 102 retrieves a date associated with the test, the test result value indicating the outcome of the test, and the test range for interpreting the test.

The lab test management system 102 may also retrieve chart template data associated with the test type (operation 908) for use in generating a graphical representation of the historical test result data. In general, chart templates include various values and parameters for related to the overall layout and style of a chart associated with the test type. For example and without limitation, such values and parameters may correspond to margins of the chart and the size, placement, color, and content of various textual or graphical elements of a chart associated with the test type.

The chart template may further specify the total range of displayable values for the chart and a chart subrange corresponding to a portion of the total range. In at least certain implementations, the total range may generally correspond to the visually displayed range of the vertical axis of the chart while the chart subrange corresponds to a portion of the vertical axis. As noted above in the context of FIGS. 7 and 8, charts in accordance with the present disclosure may include bands or similar visual elements for use in interpreting test results and which correspond to portions of the total range of the chart. For example, the chart 700 of FIG. 7 includes three visually distinct bands 710A-710C corresponding to low, normal, and high test results. Similarly, the chart 800 of FIG. 8 includes two bands 810A, 810B which may correspond to low and normal (or normal and high) test results. In such implementations, the chart subrange may generally correspond to any of the bands; however, for purposes of the current example, the chart subrange is assumed to correspond to a normal band for the test.

Each of the total range and the chart subrange may be defined in various ways. In one example implementation, each of the total range and the chart subrange for a given chart template may be predefined. For example, the total range of the chart may be defined as 100 units ranging from 0-100 and the chart subrange may be from 50-70.

In other implementations, the total range and/or the chart subrange may be based, at least in part, on the retrieved historical test data. In one such implementation, the total range may be determined based on the range of the retrieved test result values such that all test result values will be displayed on the chart. For example, a given test type for a patient may include test result values of 15, 20, 100, and 80, such that the range of the test result values is 85 units ranging from 15-100. In such an implementation, the total range of the chart may be dynamically determined to be 85 units plus a margin for visual clarity (e.g., a 10 unit margin may be applied to either end of the 85 unit range such that the total range is from 5 to 110 units).

The chart subrange may also be dynamically generated based on the historical test result data and, in particular, the test ranges of the relevant historical test result data. For example, in one implementation, the chart subrange may be chosen as the narrowest or broadest test range of the relevant historical test result data. In another implementation, the chart subrange may include the lowest (or highest) lower bound of the relevant test ranges and the highest (or lowest) upper bound, of the relevant test ranges. In still other implementations, the chart subrange may be selected as the oldest or most recent test range received by the lab test management system 102. In yet other implementations, the chart subrange may be calculated as some mathematical combination (e.g., an average) of the relevant test ranges.

In still other implementations, the total range of the chart may be determined based on the chart subrange, which in turn may be predetermined or dynamically determined based on the historical test result data. For example, in a three-band chart, the total chart range may be determined such that the chart subrange is displayed as the middle third (or other predetermined portion) of the chart. In such cases, the chart subrange may be defined first and then the total range of the chart may be calculated based on the chart subrange.

It should be appreciated that in at least some cases, the test range may be unbounded. For example, a test may exist where any test result value above 50 units is considered normal or healthy. In such cases, the corresponding test range in the test result data may simply include the lower threshold of 50 units or may specify that the acceptable range for the test is 50 units to infinity. To address such situations, the total range of the chart may be chosen such that the lower bound of the test range occupies a particular location within the chart. For example, in one specific implementation, the lower bound may be disposed at the midpoint of the chart. So, for a test range with a lower bound of 50 units, the total range of the chart would be 100 units ranging from 0-100 units such that the lower bound of 50 units is located in the middle of the chart.

Unbounded test ranges may be resolved in other ways. For example, in certain cases only some test results will include unbounded ranges while other test results will include a bounded range. Accordingly, the system 102 may automatically select one or more of the bounded ranges as the basis for determining the total range of the chart. In still other implementations, each test type may be given a predetermined maximum value in the event of unbounded test ranges.

Subsequent to retrieving the historical test result data and the chart template data, the lab test management system 102 may generate graphical data for rendering and displaying a corresponding chart at the requesting device (operation 910). The graphical data generated by the lab test management system 102 may generally include data for rendering and displaying chart elements (e.g., axes, labels, chart subranges, etc. included in the chart template data or dynamically generated, as discussed above) as well as data indicating the location of indicators within the chart corresponding to the relevant test result values.

As noted above, each test result displayed in the chart may generally be represented by a visual indicator, such as a circle. The lab test management system 102 determines the location of each indicator with respect to the total range of the chart based on the test result value and the test range for each indicator to be displayed. More specifically, the lab test management system 102 applies scaling and offsetting operations to fit the test range for the test result associated with the indicator to the chart subrange and the places the indicator accordingly.

Although various approaches may be implemented to determine the location of a given indicator, in at least one implementation, the location of a particular indicator may be determined using equation (1):

$$x_{chart} = \frac{(x_{test} - B_{test})}{R_{test}/R_{chart}} + B_{chart} \qquad (1)$$

where $x_{chart}$ is the location of the indicator relative to the total range of the chart, $x_{test}$ is the test result value, $B_{test}$ is a value corresponding to a boundary of the test range (e.g., a lower or upper boundary), $R_{test}$ is the magnitude of the test range, $R_{chart}$ is the magnitude of the chart subrange, and $B_{chart}$ is the value of the chart subrange corresponding to the equivalent of $B_{test}$ of the chart (e.g., a lower bound or upper bound of the chart subrange). More generally, equation (1) normalizes the test result data to the range of the chart. To do so, the difference between the test result value and a boundary of the test range is scaled according to the ratio of the test range to the chart subrange and the result is then offset based on a boundary of the chart.

Generating the graphical data includes executing the foregoing (or similar) operation for each test result value using its respective test range information. Accordingly, each test result value is uniquely fit to the chart based on its underlying test result data, thereby taking into account any discrepancies or variations in the test ranges of the test result data. A more detailed example of locating each indicator of the chart is provided below in the context of FIG. 11.

Subsequent to generating the graphical data, the lab test management system 102 may transmit the graphical data to the requesting user computing device for rendering and display at the user computing device (operation 912).

As illustrated in FIG. 9B, subsequent to providing the graphical data for display and rendering at the user computing device, the lab test management system 102 may receive an element selection message indicating a selection of a graphical element of the corresponding chart (operation 914). For example, a user may tap or otherwise select one of the indicators or similar graphical element displayed on the user computing device 122. In response, the user computing device 122 may generate and transmit the corresponding element selection message to the lab test management system 102.

The element selection message may include, among other things, an identifier associated with the element selected by the user. For example, each indicator displayed on the rendered and displayed chart may be associated with an identifier that is included in the element selection message and that identifies the particular indicator. Similarly, other elements of the chart (e.g., dates along the time axis, labels corresponding to bands/ranges of the chart), may similarly be selectable and may result in the generation and transmission of an element selection message to the lab test management system 102 when selected.

Upon receiving an element selection message, the lab test management system 102 retrieves data corresponding to the selected element (operation 916). For example and without limitation, in certain implementations, when the selected element is an indicator, the lab test management system 102 may retrieve the detailed lab result data (or a portion thereof) corresponding to the indicator. The lab test management system 102 may also retrieve content (e.g., audio, video, articles, etc.), such as may be stored in the content data store 118 of FIG. 1, for presentation to the user. Accordingly, following retrieval of the additional data or content, the lab test management system 102 may transmit the retrieved data or content to the user computing device 122 for presentation (operation 918).

In certain implementations, the content provided to the user may be curated or otherwise customized to the specific user based on additional information and test result data associated with the user and available at the lab test management system 102. For example, the lab test management system 102 may include a content management system that identifies and provides content based on user information including, but not limited to, the user's historical test result data.

FIG. 10 is a flow chart illustrating a complementary method 1000 to the method 900 of FIGS. 9A and 9B. More specifically, the method 1000 generally includes the steps for requesting and presenting historical lab test result data from the perspective of the user computing device 122.

Beginning at operation 1002, the user computing device 122 receives a selection of a test type from a user. For example, the user computing device 122 may execute an application (or "app"), program, website, or other software that presents a user interface to a user of the user computing device 122. As discussed above in the context of FIGS. 2A-6E, the user interface may generally allow a user to access and review test result data, educational content, and the like, made available via the lab test management system 102.

In at least certain implementations, the user interface may present a user with a list of available test types (e.g., test types for which historical test results are available). In such implementations, receiving a selection at the user computing device 122 may be the result of the user selecting one of the displayed test types (e.g., by tapping or clicking one of the displayed test types). In other implementations, selecting a test type may include navigating to a page or similar portion of the user interface configured to display historical test results for available test types.

Regardless of how a selection is made, the user computing device 122 then generates and transmits a corresponding request for historical test result data to the lab test management system 102 (operation 1004). In response, the user computing device 122 receives graphical data corresponding to a chart (operation 1006) and renders and displays the graphical data to display the chart (operation 1008). As discussed in the context of FIG. 9, above, the graphical data includes, among other things, parameters for defining various elements of the chart as well as data corresponding to the location of one or more test result value indicators to be displayed on the chart. Also as noted above, the location data is generated by the lab test management system 102, in part, by fitting test range data for each test result to be displayed to a chart subrange of the chart, each of the test range and the chart subrange corresponding to a range of interest, such as a health or normal range for the particular test.

Subsequent to rendering and displaying the chart, the user computing device 122 may receive another selection corresponding to a graphical element of the chart displayed to the user (operation 1010). In response, the user computing device 122 may generate and transmit an element selection message to the lab test management system 102 (operation 1012) requesting additional data and/or educational content. As discussed above and by way of non-limiting example only, the additional data may include more detailed test result data associated with, e.g., a selected indicator or educational content relevant to the selected element, including customized or curated content selected by a content management system based on user data. Accordingly, in response to transmitting the element selection message, the user computing device 122 receives and displays the additional data or curated content (operation 1014).

Figure 11:
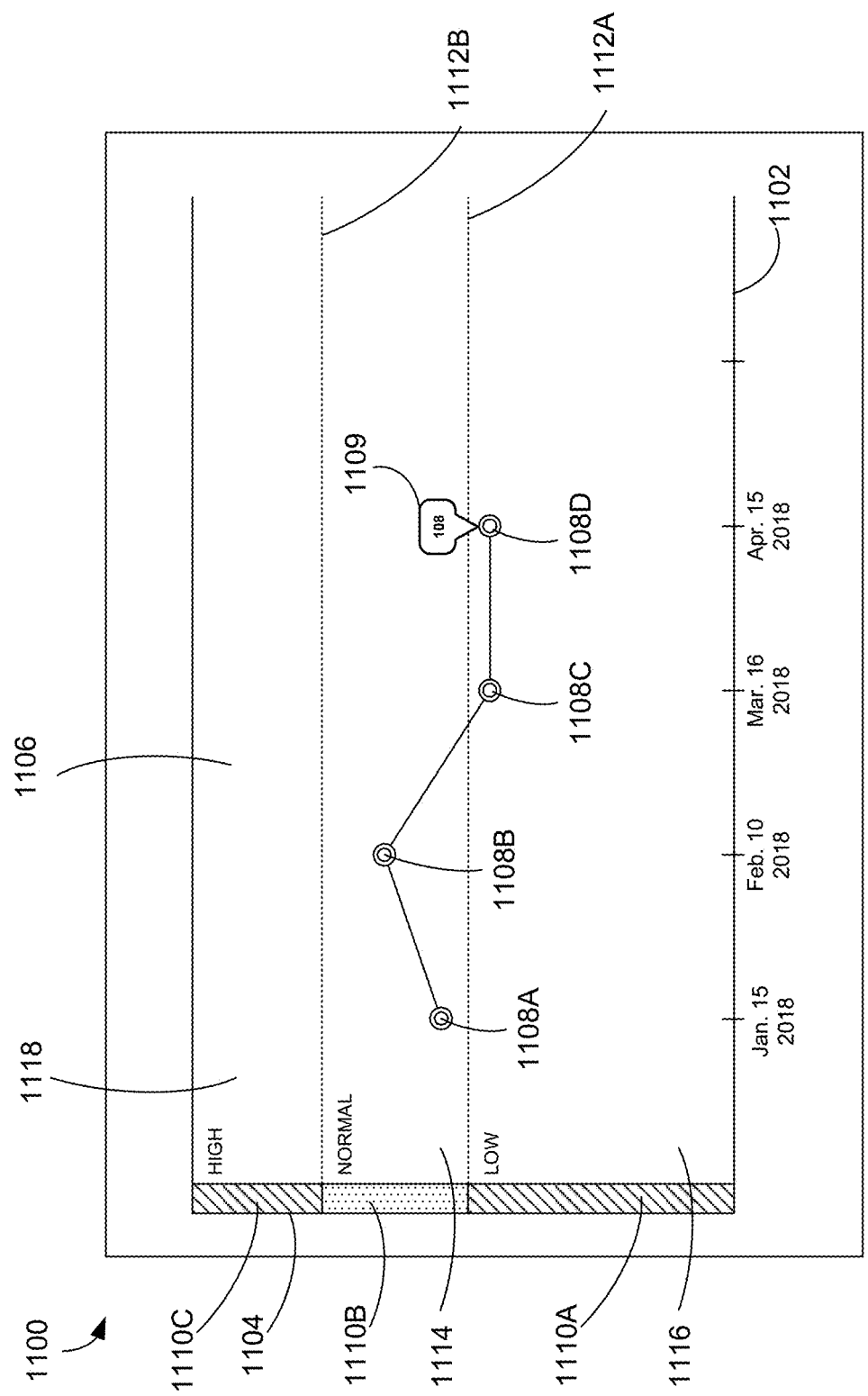
FIG. 11 is a third example chart including historical test result data and according to the present disclosure.

To further explain some of the foregoing concepts and additional aspects of implementations of the present disclosure, FIG. 11 is provided. FIG. 11 illustrates an example chart 1100 for displaying historical test result data and which may be generated and displayed using systems and methods disclosed herein. The chart 1100 includes a horizontal axis 1102 indicating time/date and a vertical axis 1104 indicating test result value. The horizontal axis 1102 and the vertical axis 1104 generally define a display area 1106 within which indicators 1108A-1108D corresponding to test result values are placed.

As shown in FIG. 11, one or more of the indicators 1108A-1108D may include a corresponding callout 1109 including the underlying test result value. Although a callout may be applied to any or all of the indicators, in at least one implementation, a callout is applied to only the most recent test result value to avoid confusion when the same test result value may result in indicators being placed at different locations within the display area 1106 (e.g., the January and February entries in Table 1, below).

As previously discussed in the context of FIG. 9, charts in accordance with the present disclosure generally include each of a total range corresponding to the full range of displayable test result values and a chart subrange corresponding to a portion of the total range. For example, in certain implementations, the chart subrange may correspond to a "normal" or healthy range of test result values for the particular test type.

To facilitate interpretation of the historical test result data displayed in the chart 1100, the chart 1100 may include various visual elements for delineating the chart subrange from the total range. For example, the chart 1100 includes both vertical bars 1110A-1110C and horizontal lines 1112A, 1112B for visually identifying and delineating the chart subrange 1114 (indicated in the chart as being a "normal" range) from other ranges displayed in the chart, namely a low range 1116 and a high range 1118.

As previously discussed in the context of FIGS. 9A-9B, charts in accordance with the present disclosure are generated, in part, by fitting test result data to a common chart. More specifically, such fitting is between test ranges included in the test result data and a chart subrange of the chart.

For illustrative purposes only, the chart of FIG. 11 is assumed to have a total range of 100 units ranging from 0-100 and a chart subrange of 25 units ranging from 50-75 units. The locations of each indicator 1108A-1108D were subsequently determined using equation (1), above, and using the example test result data shown below in Table 1.

TABLE 1

Example Test Results and Corresponding Chart Locations

| Test Date | Test Result Value | Test Range | Chart Location |
|---|---|---|---|
| Jan. 15, 2018 | 110 | 100-150 (50 units) | 55 (normal) |
| Feb. 10, 2018 | 110 | 90-120 (30 units) | 67 (normal) |
| Mar. 16, 2018 | 95 | 100-150 (50 units) | 47.5 (low) |
| Apr. 15, 2018 | 108 | 110-130 (20 units) | 47.5 (low) |

While the variations in the test ranges included in Table 1 may be exaggerated for effect, various pieces of important information are provided by the chart 1100 that would not be readily apparent otherwise. For example, as indicated in the data of Table 1, each of the January and February tests had the same test result value (110 units). Due to different test ranges, the February test was generally an improvement as that test result was more centralized within the corresponding test range for that specific test. While such a distinction may be lost by looking only at the test result values, it is clearly indicated by the difference in indicator 1108A and 1108B in the chart 1100. Conversely, while the test result value between March and April increased, suggesting an improvement, variations between the corresponding test ranges reveal that the increase did not move the patient any closer a normal test value, as indicated by the indicator 1108C and the indicator 1108D being at the same vertical location within the chart 1100. In other words, a patient/user considering only test result values may believe that they have exhibited an improvement when in reality any such perceived improvement is a result of differences in the underlying test ranges. Again, the approach in generating the chart 1100 avoids such misinterpretation.

While discussed herein in the context of analyzing and interpreting lab test results, it should be appreciated that the present disclosure may be applied more broadly, including in medical-related areas outside of lab test results and even applications outside of the medical field entirely. More generally, the present disclosure describes methods and systems for aggregating and presenting test data for which a range of interest may vary from test-to-test. To address such variability, the approach disclosed herein includes normalizing the variable ranges of interest (e.g., a "normal" range) for each test to a predefined range (e.g., the chart subrange discussed above) and then presenting the normalized test data with respect to the predefined range. Doing so greatly simplifies interpretation of the test results as a user can readily determine whether and to what degree a given test result is considered to be within the range of interest.

Figure 12:
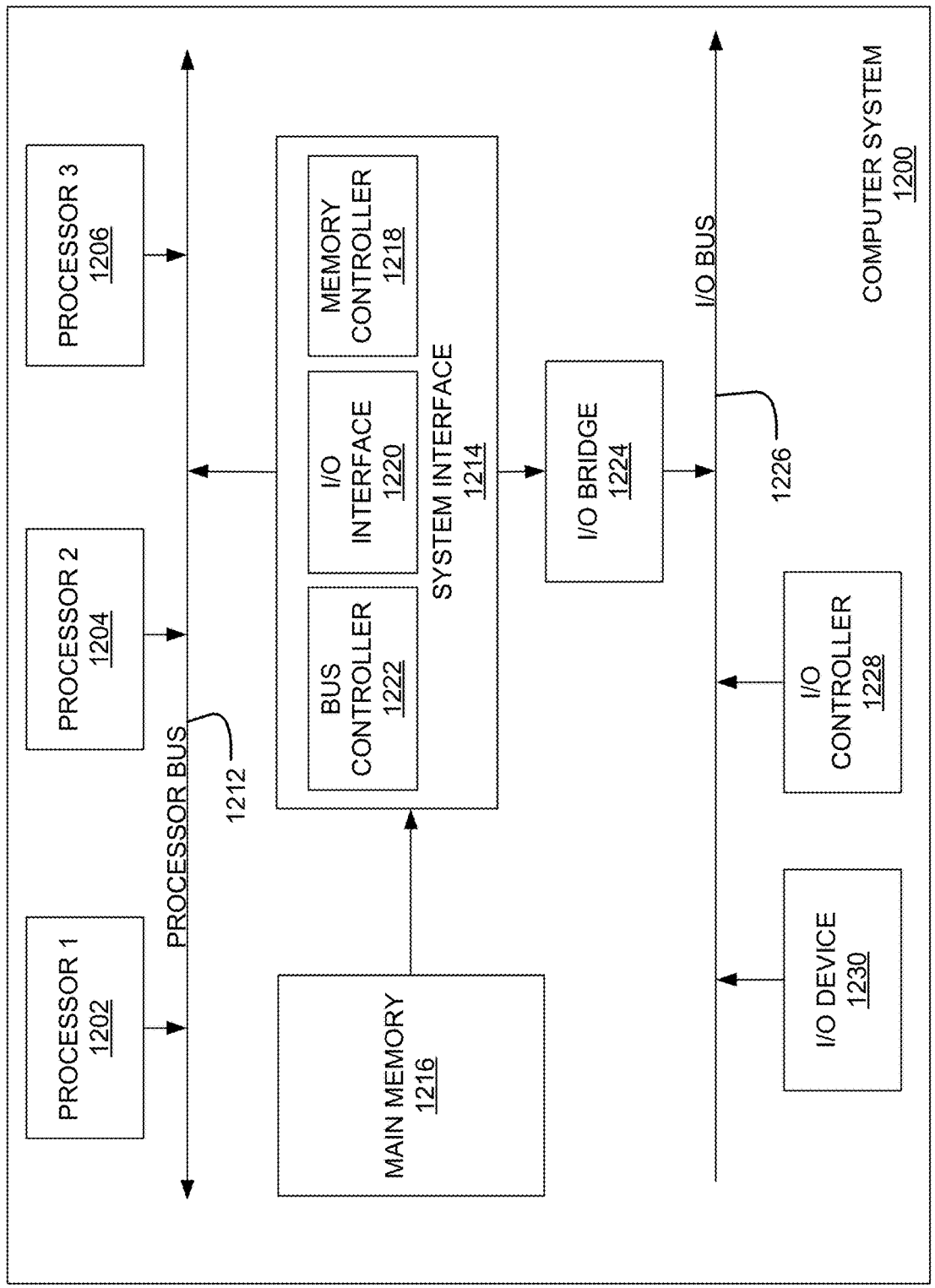
FIG. 12 is a diagram illustrating an example of a computing system which may be used in implementing embodiments of the present disclosure.

FIG. 12 is a block diagram illustrating an example of a computing device or computer system 1200 which may be used in implementing the embodiments of the components of the system disclosed above. The computer system (system) includes one or more processors 1202-1206. Processors 1202-1206 may include one or more internal levels of cache (not shown) and a bus controller or bus interface unit to direct interaction with the processor bus 1212. Processor bus 1212, also known as the host bus or the front side bus, may be used to couple the processors 1202-1206 with the system interface 1214. System interface 1214 may be connected to the processor bus 1212 to interface other components of the system 1200 with the processor bus 1212. For example, system interface 1214 may include a memory controller 1218 for interfacing a main memory 1216 with the processor bus 1212. The main memory 1216 typically includes one or more memory cards and a control circuit (not shown). System interface 1214 may also include an input/output (I/O) interface 1220 to interface one or more I/O bridges or I/O devices with the processor bus 1212. One or more I/O controllers and/or I/O devices may be connected with the I/O bus 1226, such as I/O controller 1228 and I/O device 1230, as illustrated. The system interface 1214 may further include a bus controller 1222 to interact with processor bus 1212 and/or I/O bus 1226.

I/O device 1230 may also include an input device (not shown), such as an alphanumeric input device, including alphanumeric and other keys for communicating information and/or command selections to the processors 1202-1206. Another type of user input device includes cursor control, such as a mouse, a trackball, or cursor direction keys for communicating direction information and command selections to the processors 1202-1206 and for controlling cursor movement on the display device.

System 1200 may include a dynamic storage device, referred to as main memory 1216, or a random access memory (RAM) or other computer-readable devices coupled to the processor bus 1212 for storing information and instructions to be executed by the processors 1202-1206. Main memory 1216 also may be used for storing temporary variables or other intermediate information during execution of instructions by the processors 1202-1206. System 1200 may include a read only memory (ROM) and/or other static storage device coupled to the processor bus 1212 for storing static information and instructions for the processors 1202-1206. The system set forth in FIG. 12 is but one possible example of a computer system that may employ or be configured in accordance with aspects of the present disclosure.

According to one embodiment, the above techniques may be performed by computer system 1200 in response to processor 1204 executing one or more sequences of one or more instructions contained in main memory 1216. These instructions may be read into main memory 1216 from another machine-readable medium, such as a storage device. Execution of the sequences of instructions contained in main memory 1216 may cause processors 1202-1206 to perform the process steps described herein. In alternative embodiments, circuitry may be used in place of or in combination with the software instructions. Thus, embodiments of the present disclosure may include both hardware and software components.

A machine readable medium includes any mechanism for storing or transmitting information in a form (e.g., software, processing application) readable by a machine (e.g., a computer). Such media may take the form of, but is not limited to, non-volatile media and volatile media. Non-volatile media includes optical or magnetic disks. Volatile media includes dynamic memory, such as main memory 1216. Common forms of machine-readable medium may include, but is not limited to, magnetic storage medium; optical storage medium (e.g., CD-ROM); magneto-optical storage medium; read only memory (ROM); random access memory (RAM); erasable programmable memory (e.g., EPROM and EEPROM); flash memory; or other types of medium suitable for storing electronic instructions.

Embodiments of the present disclosure include various steps, which are described in this specification. The steps may be performed by hardware components or may be embodied in machine-executable instructions, which may be used to cause a general-purpose or special-purpose processor programmed with the instructions to perform the steps. Alternatively, the steps may be performed by a combination of hardware, software, and/or firmware.

The description above includes example systems, methods, techniques, instruction sequences, and/or computer program products that embody techniques of the present disclosure. However, it is understood that the described disclosure may be practiced without these specific details. In the present disclosure, the methods disclosed may be implemented as sets of instructions or software readable by a device. Further, it is understood that the specific order or hierarchy of steps in the methods disclosed are instances of example approaches. Based upon design preferences, it is understood that the specific order or hierarchy of steps in the method can be rearranged while remaining within the disclosed subject matter. The accompanying method claims present elements of the various steps in a sample order, and are not necessarily meant to be limited to the specific order or hierarchy presented.

It is believed that the present disclosure and many of its attendant advantages should be understood by the foregoing description, and it should be apparent that various changes may be made in the form, construction, and arrangement of the components without departing from the disclosed subject matter or without sacrificing all of its material advantages. The form described is merely explanatory, and it is the intention of the following claims to encompass and include such changes.

While the present disclosure has been described with reference to various embodiments, it should be understood that these embodiments are illustrative and that the scope of the disclosure is not limited to them. Many variations, modifications, additions, and improvements are possible. More generally, embodiments in accordance with the present disclosure have been described in the context of particular implementations. Functionality may be separated or combined in blocks differently in various embodiments of the disclosure or described with different terminology. These and other variations, modifications, additions, and improvements may fall within the scope of the disclosure as defined in the claims that follow.

What is claimed is:

1. A method of providing test results, the method comprising:
    receiving, at a computing system and from a user computing device, a request for historical test result data associated with a patient, the request including a test type;
    at the computing system and in response to receiving the request, accessing historical test result data associated with the patient for the test type, the historical test result data including a first test result value for a first test of the test type, a first test range for the first test, a second test result value for a second test of the test type, and a second test range for the second test, wherein:
        the first test range is different from the second test range, and
        at least a portion of the historical test result data corresponds to test result data received through a translation layer between the computing system and a healthcare data system, and wherein the translation layer converts the test result data into a common format for storage in one or more data sources of the computing system;
    accessing, using the computing system, chart data associated with the test type, the chart data including a total chart range and a chart subrange, the chart subrange being a portion of the total chart range;
    generating, at the computing system, graphical data for displaying the historical test result data in a chart at the user computing device, wherein generating the graphical data comprises:
        calculating a first location for displaying a first indicator for the first test result value relative to the total chart range, and
        calculating a second location for displaying a second indicator for the second test result value relative to the total chart range, wherein calculating each of the first location and the second location comprises normalizing the historical test result data of the first test and the second test by fitting each of the first test range and the second test range to the chart subrange; and
    transmitting the graphical data from the computing system to the user computing device for rendering and display at the user computing device,
    wherein calculating the first location and fitting of the first test range to the chart subrange are performed using the following equation:

$$x_{chart} = \frac{(x_{test} - B_{test})}{R_{test}/R_{chart}} + B_{chart}$$

where:
    $x_{chart}$ is the first location relative to the total chart range,
    $x_{test}$ is the first test result value,
    $R_{test}$ is a magnitude of the first test range,
    $R_{chart}$ is a magnitude of the chart subrange,
    $B_{test}$ is a threshold value for the first test range, and
    $B_{chart}$ is a threshold value for the chart subrange corresponding to the threshold value for the first test range.

2. The method of claim 1, further comprising:
    receiving the test result data at the computing system from the healthcare data system; and
    storing the test result data in the one or more data sources of the computing system as part of the historical test result data;
    wherein the test result data is received through the translation layer between the computing system and the healthcare data system.

3. The method of claim 1, wherein each of the first test range and the chart subrange correspond to a normal result range for the test type.

4. The method of claim 1, wherein the chart subrange corresponds to an intermediate range of the total chart range such that the chart includes at least three visually delineated ranges, the at least three visually delineated ranges including a first visually delineated range corresponding to the chart subrange, a second visually delineated range corresponding to values below the first visually delineated range, and a third visually delineated range corresponding to values above the first visually delineated range.

5. The method of claim 1, wherein the chart subrange corresponds to one of an upper range and a lower range of the total chart range such that the chart includes at least two visually delineated ranges, the at least two visually delineated ranges including a first visually delineated range corresponding to the chart subrange and a second visually delineated range corresponding to values above the first visually delineated range when the chart subrange is the lower range or values below the first visually delineated range when the chart subrange is the upper range.

6. The method of claim 1 further comprising:
subsequent to transmitting the graphical data to the user computing device, receiving, at the computing system and from the user computing device, a message including an identifier corresponding to a graphical element of the chart; and
in response to receiving the message, transmitting from the computing system, at least one of additional test result data corresponding to the test or content associated with the test to the user computing device.

7. A computing system comprising:
one or more processors; and
a memory storing instructions executable by the one or more processors, wherein, when executed by the one or more processors, the instructions cause the one or more processors to:
receive, from a user computing device, a request for historical test result data associated with a patient, the request including a test type;
in response to receiving the request, access historical test result data associated with the patient for the test type, the historical test result data including a first test result value for a first test of the test type, a first test range for the first test, a second test result value for a second test of the test type, and a second test range for the second test, wherein:
the first test range is different from the second test range, and
at least a portion of the historical test result data corresponds to test result data received through a translation layer between the computing system and a healthcare data system, and wherein the translation layer converts the test result data into a common format for storage in one or more data sources of the computing system;
access chart data associated with the test type, the chart data including a total chart range and a chart subrange, the chart subrange being a portion of the total chart range;
generate graphical data for displaying the historical test result data in a chart at the user computing device, wherein generating the graphical data includes:
calculating a first location for displaying first indicator for the first test result value relative to the total chart range, and
calculating a second location for displaying a second indicator for the second test result value relative to the total chart range, wherein calculating each of the first location and the second location comprises normalizing the historical test result data of the first test and the second test by fitting each of the first test range and the second test range to the chart subrange; and
transmit the graphical data from the computing system to the user computing device for rendering and display at the user computing device,
wherein calculating the first location and fitting of the first test range to the chart subrange are performed using the following equation:

$$x_{chart} = \frac{(x_{test} - B_{test})}{R_{test}/R_{chart}} + B_{chart}$$

where:
$x_{chart}$ is the first location relative to the total chart range,
$x_{test}$ is the first test result value,
$R_{test}$ is a magnitude of the first test range,
$R_{chart}$ is a magnitude of the chart subrange,
$B_{test}$ is a threshold value for the first test range, and
$B_{chart}$ is a threshold value for the chart subrange corresponding to the threshold value for the first test range.

8. The computing system of claim 7, wherein each of the first test range and chart subrange correspond to a normal result for the test type.

9. A method of accessing and displaying test results, the method comprising:
transmitting, from a user computing device, a request for historical test result data associated with a patient to a remote computing system, the request including a test type, wherein at least a portion of the historical test result data corresponds to test result data received through a translation layer between the remote computing system and a healthcare data system, and wherein the translation layer converts the test result data into a common format for storage in one or more data sources of the computing system;
receiving, at the user computing device and from the remote computing system, graphical data for rendering and displaying a chart of the historical test result data, wherein:
the graphical data is generated by the remote computing device,
the graphical data includes:
a first indicator location for displaying a first indicator relative to a total chart range of a chart, the first indicator corresponding to a first test result value of a first test included in the historical test result data,
a second indicator location for displaying a second indicator relative to the total chart range, the second indicator corresponding to a second test result value of a second test included in the historical test result data,
the first indicator location is calculated by the remote computing device by normalizing the historical test result data of the first test by fitting a first test range corresponding to the first test to a chart subrange of the chart, the chart subrange being a portion of a total chart range of the chart corresponding to the test range, and
the second indicator location is calculated by the remote computing device by normalizing the historical test result data of the second test by fitting a second test range corresponding to the second test and different from the first test range to the chart subrange; and
in response to receiving the graphical data, rendering the graphical data using the user computing device to display the chart on a display of the user computing device, the chart including the first indicator at the first indicator location and the second indicator at the second indicator location,
wherein the remote computing device calculates the location of the first indicator and fits the first test range to the chart subrange using the following equation:

$$x_{chart} = \frac{(x_{test} - B_{test})}{R_{test} / R_{chart}} + B_{chart}$$

where:
- $x_{chart}$ is the location of the indicator relative to the total chart range,
- $x_{test}$ is the first test result value,
- $R_{test}$ is a magnitude of the first test range,
- $R_{chart}$ is a magnitude of the chart subrange,
- $B_{test}$ is a threshold value for the first test range, and
- $B_{chart}$ is a threshold value for the chart subrange corresponding to the threshold value for the first test range.

10. The method of claim 9, wherein rendering the graphical data further includes displaying a most recent test result value adjacent a most recent indicator.

11. The method of claim 9, wherein the chart includes a plurality of visually delineated ranges, one of the visually delineated ranges corresponding to the chart subrange.

12. The method of claim 9 further comprising:
- receiving a selection of a graphical element of the chart at the user computing device, the graphical element associated with a test;
- transmitting, in response to receiving the selection, a request to the remote computing device including an identifier associated with the graphical element; and
- receiving, from the remote computing device, at least one of additional details of test and informational content selected by the remote computing device.

13. A method of providing test results, the method comprising:
- receiving, at a computing system and from a user computing device, a request for historical test result data associated with a patient, the request including a test type;
- at the computing system and in response to receiving the request, accessing historical test result data associated with the patient for the test type, the historical test result data including a test result value for a test of the test type and a test range for the test, wherein at least a portion of the historical test result data corresponds to test result data received through a translation layer between the computing system and a healthcare data system, and wherein the translation layer converts the test result data into a common format for storage in one or more data sources of the computing system;
- accessing, using the computing system, chart data associated with the test type, the chart data including a total chart range and a chart subrange, the chart subrange being a portion of the total chart range corresponding to the test range;
- generating, at the computing system, graphical data for displaying the historical test result data at the user computing device, wherein generating the graphical data comprises calculating a location for displaying an indicator for the test result value relative to the total chart range, and wherein calculating the location comprises normalizing the historical test result data of the test by fitting the test range to the chart subrange; and
- transmitting the graphical data from the computing system to the user computing device for rendering and display at the user computing device,
- wherein calculating the location of the indicator and fitting of the test range to the chart subrange are performed using the following equation:

$$x_{chart} = \frac{(x_{test} - B_{test})}{R_{test} / R_{chart}} + B_{chart}$$

where:
- $x_{chart}$ is the location of the indicator relative to the total chart range,
- $x_{test}$ is the test result value,
- $R_{test}$ is a magnitude of the test range,
- $R_{chart}$ is a magnitude of the chart subrange,
- $B_{test}$ is a threshold value for the test range, and
- $B_{chart}$ is a threshold value for the chart subrange corresponding to the threshold value for the test range.

* * * * *